US010723913B2

(12) United States Patent
Zhou et al.

(10) Patent No.: US 10,723,913 B2
(45) Date of Patent: Jul. 28, 2020

(54) HYDROXY FUNCTIONAL ALKYL POLYUREA CONTAINING COMPOSITIONS

(71) Applicant: PPG Industries Ohio, Inc., Cleveland, OH (US)

(72) Inventors: Hongying Zhou, Allison Park, PA (US); Shanti Swarup, Allison Park, PA (US); Anthony M. Chasser, Greensburg, PA (US); Edward R. Millero, Jr., Gibsonia, PA (US); John R. Schneider, Allison Park, PA (US); Tien-Chieh Chao, Mars, PA (US); Christopher P. Kurtz, Millvale, PA (US); Xiangling Xu, Pittsburgh, PA (US); John M. Dudik, Apollo, PA (US); William H. Retsch, Jr., Allison Park, PA (US); Benjamin Kabagambe, Pittsburgh, PA (US); Ronald Kralic, Beaver Falls, PA (US)

(73) Assignee: PPG Industries Ohio, Inc., Cleveland, OH (US)

( * ) Notice: Subject to any disclaimer, the term of this patent is extended or adjusted under 35 U.S.C. 154(b) by 0 days.

(21) Appl. No.: 16/069,785

(22) PCT Filed: Jan. 13, 2017

(86) PCT No.: PCT/US2017/013340
§ 371 (c)(1),
(2) Date: Jul. 12, 2018

(87) PCT Pub. No.: WO2017/123873
PCT Pub. Date: Jul. 20, 2017

(65) Prior Publication Data
US 2019/0016918 A1    Jan. 17, 2019

Related U.S. Application Data

(63) Continuation of application No. 14/996,838, filed on Jan. 15, 2016, now abandoned.

(51) Int. Cl.
| | |
|---|---|
| C09D 175/12 | (2006.01) |
| C09D 5/02 | (2006.01) |
| C09D 5/03 | (2006.01) |
| B27N 7/00 | (2006.01) |
| C08G 18/48 | (2006.01) |
| C08G 18/66 | (2006.01) |
| C08G 18/67 | (2006.01) |
| C08G 18/75 | (2006.01) |
| C08G 18/79 | (2006.01) |
| C08G 18/80 | (2006.01) |
| C08G 18/24 | (2006.01) |
| C09D 175/16 | (2006.01) |
| C08G 18/32 | (2006.01) |
| C08G 18/34 | (2006.01) |
| C09D 175/02 | (2006.01) |
| B65D 1/12 | (2006.01) |
| C07C 275/14 | (2006.01) |
| C07C 275/26 | (2006.01) |
| C08G 18/73 | (2006.01) |
| B27N 3/00 | (2006.01) |

(52) U.S. Cl.
CPC .......... *C09D 175/12* (2013.01); *B27N 7/005* (2013.01); *B65D 1/12* (2013.01); *C07C 275/14* (2013.01); *C07C 275/26* (2013.01); *C08G 18/246* (2013.01); *C08G 18/3275* (2013.01); *C08G 18/348* (2013.01); *C08G 18/48* (2013.01); *C08G 18/4854* (2013.01); *C08G 18/6692* (2013.01); *C08G 18/672* (2013.01); *C08G 18/73* (2013.01); *C08G 18/751* (2013.01); *C08G 18/755* (2013.01); *C08G 18/792* (2013.01); *C08G 18/8041* (2013.01); *C09D 5/02* (2013.01); *C09D 5/03* (2013.01); *C09D 175/02* (2013.01); *C09D 175/16* (2013.01); *B27N 3/002* (2013.01)

(58) Field of Classification Search
CPC .......... C09D 175/12; C09D 5/02; C09D 5/03; C09D 175/16; C09D 175/02; B27N 7/005; B27N 3/002; C08G 18/4854; C08G 18/6692; C08G 18/672; C08G 18/755; C08G 18/792; C08G 18/8041; C08G 18/246; C08G 18/3275; C08G 18/348; C08G 18/73; C08G 18/751; C08G 18/48; C07C 275/14; C07C 275/26; B65D 1/12
See application file for complete search history.

(56) References Cited

U.S. PATENT DOCUMENTS

| | | |
|---|---|---|
| 3,294,751 A | 12/1966 | Beitchman |
| 3,420,787 A | 1/1969 | Reymore et al. |
| 3,663,516 A | 5/1972 | Vogt |
| 4,211,683 A | 7/1980 | Wenzel |
| 4,284,572 A | 8/1981 | Stanley et al. |
| 4,990,579 A | 5/1991 | Paar |
| 5,030,754 A | 7/1991 | Speranza et al. |

(Continued)

FOREIGN PATENT DOCUMENTS

| | | |
|---|---|---|
| CN | 1662618 A | 8/2005 |
| CN | 101098935 A | 1/2008 |

(Continued)

OTHER PUBLICATIONS

Machine English translation of CN101098935.

(Continued)

*Primary Examiner* — Michael C Miggins
(74) *Attorney, Agent, or Firm* — Diane R. Meyers

(57) ABSTRACT

Compositions comprising hydroxy functional alkyl polyureas are disclosed.

27 Claims, 1 Drawing Sheet

(56) References Cited

U.S. PATENT DOCUMENTS

| | | | |
|---|---|---|---|
| 5,047,294 | A | 9/1991 | Schwab et al. |
| 5,574,083 | A | 11/1996 | Brown et al. |
| 5,714,539 | A | 2/1998 | Perez et al. |
| 5,858,549 | A | 1/1999 | Kielbania, Jr. et al. |
| 5,965,466 | A | 10/1999 | Rodrigues et al. |
| 6,051,646 | A | 4/2000 | Nass et al. |
| 6,140,388 | A | 10/2000 | Nass et al. |
| 6,181,311 | B1 | 1/2001 | Hashimoto |
| 6,248,819 | B1 | 6/2001 | Masuda et al. |
| 6,290,867 | B1 | 9/2001 | Kielbania, Jr. et al. |
| 6,875,800 | B2 | 4/2005 | Vanier et al. |
| 6,894,086 | B2 | 5/2005 | Munro et al. |
| 7,033,526 | B2 | 4/2006 | Figiel et al. |
| 7,605,194 | B2 | 10/2009 | Ferencz et al. |
| 8,153,344 | B2 | 4/2012 | Faler et al. |
| 8,846,156 | B2 | 9/2014 | Swarup et al. |
| 2004/0266921 | A1 | 12/2004 | Rodrigues et al. |
| 2005/0113269 | A1 | 5/2005 | Landa et al. |
| 2005/0171300 | A1 | 8/2005 | Moens et al. |
| 2008/0004361 | A1 | 1/2008 | Palermo |
| 2009/0197202 | A1 | 8/2009 | Matsumura |
| 2009/0246343 | A1 | 10/2009 | Wu et al. |
| 2011/0070372 | A1 | 3/2011 | Faucher et al. |
| 2011/0070374 | A1 | 3/2011 | Ambrose et al. |
| 2011/0151128 | A1 | 6/2011 | Boggs et al. |
| 2011/0244157 | A1 | 10/2011 | Singer et al. |
| 2014/0011018 | A1 | 1/2014 | Diehl et al. |
| 2014/0023782 | A1 | 1/2014 | Kunz et al. |
| 2014/0030535 | A1 | 1/2014 | Makotky et al. |
| 2015/0225339 | A1 | 8/2015 | Niedermair et al. |
| 2015/0344732 | A1 | 12/2015 | Witt-Sanson et al. |
| 2016/0280951 | A1 | 9/2016 | Drumright et al. |

FOREIGN PATENT DOCUMENTS

| | | |
|---|---|---|
| CN | 102296290 A | 12/2011 |
| CN | 103145588 A | 6/2013 |
| CN | 103502354 A | 1/2014 |
| CN | 104955911 A | 9/2015 |
| EP | 0519186 A1 | 12/1992 |
| EP | 0866082 A1 | 9/1998 |
| EP | 1525274 B1 | 4/2005 |
| EP | 1541640 A1 | 6/2005 |
| EP | 1935878 A1 | 6/2008 |
| EP | 2316868 A1 | 5/2011 |
| EP | 2447059 A2 | 5/2012 |
| EP | 2746353 A1 | 6/2014 |
| EP | 2773710 B1 | 4/2016 |
| JP | H11335594 A | 12/1999 |
| JP | 2001192609 A | 7/2001 |
| JP | 5146327 B2 | 2/2013 |
| JP | 2014148618 A | 8/2014 |
| RU | 2376284 C1 | 10/2009 |
| RU | 2009103017 A | 8/2010 |
| WO | 2004000958 A1 | 12/2003 |
| WO | 2006132910 A1 | 12/2006 |
| WO | 2008076669 A1 | 6/2008 |
| WO | 2009095471 A1 | 8/2009 |
| WO | 2011019840 A1 | 2/2011 |
| WO | 2012118500 A1 | 9/2012 |
| WO | 2012118501 A1 | 9/2012 |
| WO | 2012162301 A1 | 11/2012 |
| WO | 2013191825 A1 | 12/2013 |
| WO | 2014025411 A1 | 2/2014 |
| WO | 2015077687 A1 | 5/2015 |

OTHER PUBLICATIONS

Machine English translation of CN103145588.
Machine English translation of EP0519186.
Machine English translation of the Abstract only of JP2001192609.
Machine English translation of JPH11335594.
Machine English translation of RU2376284.
Machine English translation of RU2009103017.

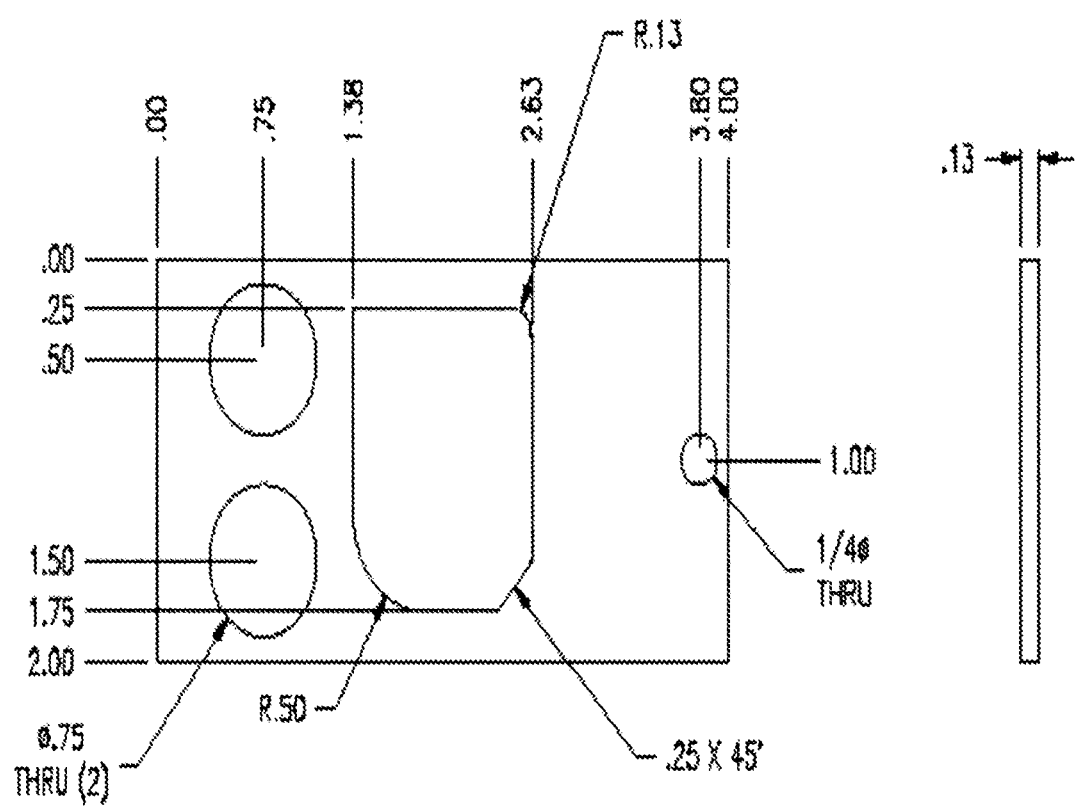

HYDROXY FUNCTIONAL ALKYL POLYUREA CONTAINING COMPOSITIONS

FIELD OF THE INVENTION

The present invention is directed to compositions that comprise a compound having a hydroxy functional alkyl polyurea and/or hydroxy functional alkyl polyurea moiety. Substrates coated at least in part with such compositions are also within the scope of the invention as are substrates formed with such compositions.

BACKGROUND OF THE INVENTION

Coatings are applied to numerous substrates to provide protective and/or decorative qualities. These coatings are often thermoset coatings, which cure upon reaction of a functional resin with a crosslinking agent having functionality that reacts with the functionality of the resin. Crosslinkers are often formaldehyde based. Many industries are interested in reducing if not eliminating formaldehyde in coatings. Coatings that are substantially, essentially or completely free of formaldehyde are desired. It is also desired by many industries to lower the temperature at which coatings cure. Additionally protective qualities provided by electrostatic modification are desirable in powder coatings on substrate areas that are normally weak.

SUMMARY OF THE INVENTION

The present invention is directed to a composition that comprises a compound comprising a hydroxy functional alkyl polyurea and/or hydroxy functional alkyl polyurea moiety having the formula:

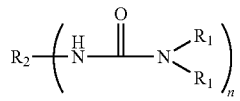

wherein $R_2$ comprises a substituted or unsubstituted $C_1$ to $C_{36}$ alkyl group, an aromatic group, an isocyanurate moiety, biuret moiety, allophonate moiety, glycoluril moiety, benzoguanamine moiety, polyetheramine moiety, and/or polymeric moiety different from a polyetheramine and having an Mn of 500 or greater; wherein each $R_1$ is independently a hydrogen, an alkyl having at least 1 carbon, or a hydroxy functional alkyl having 2 or more carbons and at least one $R_1$ is a hydroxyl functional alkyl having 2 or more carbons; and n is 2-6, and wherein the polyurea is present in the composition in an amount of 0.5 to 10 weight percent based on total solid weight. Compositions comprising a film-forming resin, a crosslinker, and a compound having a hydroxy functional alkyl polyurea and/or hydroxy functional alkyl polyurea moiety having the formula

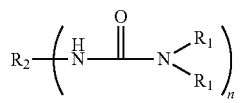

wherein $R_2$ comprises a substituted or unsubstituted $C_1$ to $C_{36}$ alkyl group, an aromatic group, an isocyanurate moiety, biuret moiety, allophonate moiety, glycoluril moiety, benzoguanamine moiety, polyetheramine moiety, and/or polymeric moiety different from a polyetheramine and having an Mn of 500 or greater; wherein each $R_1$ is independently a hydrogen, alkyl having at least 1 carbon, or a hydroxy functional alkyl having 2 or more carbons and at least one $R_1$ is a hydroxy functional alkyl having 2 or more carbons; and n is 2-6, are also within the present scope.

The present invention is also directed to a polymer or oligomer comprising a repeat unit having a hydroxy functional alkyl polyurea of the formula:

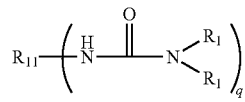

wherein $R_{11}$ is derived from a polymerizable moiety; wherein each $R_1$ is independently a hydrogen, an alkyl having at least 1 carbon, or a hydroxy functional alkyl having 2 or more carbons and at least one $R_1$ is a hydroxy functional alkyl having 2 or more carbons; and q is 1 or greater. Compositions comprising such polymers or oligomers and applications therefor are also within the scope of the present invention. Substrates coated with any of these compositions are also within the present scope.

The present invention is also directed to a substrate formed from a composition comprising: a) a composition that comprises a compound having a hydroxy functional alkyl polyurea and/or hydroxy functional alkyl polyurea moiety having the formula:

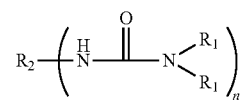

wherein $R_2$ comprises a substituted or unsubstituted $C_1$ to $C_{36}$ alkyl group, an aromatic group, an isocyanurate moiety, biuret moiety, allophonate moiety, glycoluril moiety, benzoguanamine moiety, polyetheramine moiety, and/or polymeric moiety different from a polyetheramine and having an Mn of 500 or greater; wherein each $R_1$ is independently a hydrogen, alkyl having at least 1 carbon, or a hydroxy functional alkyl having 2 or more carbons and at least one $R_1$ is a hydroxy functional alkyl having 2 or more carbons; and n is 2-6; and b) wood particles.

DETAILED DESCRIPTION OF THE INVENTION

The present invention is directed to compositions comprising a compound having a hydroxy functional alkyl polyurea compound and/or hydroxy functional alkyl polyurea moiety as described below. Such compounds can be used in various compositions including coatings, adhesives, and sealants, and can function, for example, as additives, binders and/or film-forming resins in such compositions. The hydroxyl functional alkyl polyurea compounds/moiety may have the general formula:

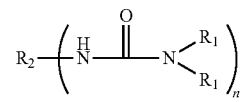

wherein $R_2$ comprises a substituted or unsubstituted $C_1$ to $C_{36}$ alkyl group, an aromatic group, an isocyanurate moiety, biuret moiety, allophonate moiety, glycoluril moiety, benzoguanamine moiety, polyetheramine moiety, and/or polymeric moiety different from a polyetheramine and having an Mn of 500 or greater; wherein each $R_1$ is independently a hydrogen, an alkyl or a hydroxy functional alkyl having 2 or more carbons and at least one $R_1$ is a hydroxy functional alkyl having 2 or more carbons; and n is 2-6, and wherein the polyurea is present in the composition in an amount of 0.5 to 10 weight percent based on total solid weight. For example, the polyurea can be present in the composition in an amount of 0.5 to 7.5 weight percent or 0.5 to 5.0 weight percent, or 1.0 to 5.0 weight percent, based on total solid weight. The $R_1$ group may exclude ether linkages. When $R_2$ comprises a substituted or unsubstituted $C_1$ to $C_{36}$ alkyl group, the composition may exclude components that would react to form urethane linkages. When $R_2$ comprises a substituted or unsubstituted $C_1$ to $C_{36}$ alkyl group, $R_2$ may contain COOH groups. $R_2$ can be acid functional. Also, it will be understood that when $R_2$ is a substituted or unsubstituted alkyl group, there may be two $R_2$ groups attached to the N, and the two $R_2$ groups may be the same or different. For example, if the hydroxy functional alkyl polyurea is formed from the reaction of dimethyl carbonate with dibutylamine and diisopropanol amine, there will be two $R_2$ groups that will each be $C_4$.

The compositions of the present invention may comprise a film-forming resin, a crosslinker, and a compound having a hydroxy functional alkyl polyurea and/or hydroxy functional alkyl polyurea moiety having the formula

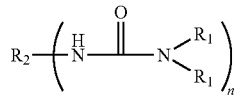

wherein $R_2$ comprises a substituted or unsubstituted $C_1$ to $C_{36}$ alkyl group, an aromatic group, an isocyanurate moiety, biuret moiety, allophonate moiety, glycoluril moiety, benzoguanamine moiety, polyetheramine moiety, and/or polymeric moiety different from a polyetheramine and having an Mn of 500 or greater; wherein each $R_1$ is independently a hydrogen, alkyl having at least 1 carbon, or a hydroxy functional alkyl having 2 or more carbons and at least one $R_1$ is a hydroxy functional alkyl having 2 or more carbons; and n is 2-6. It will be appreciated that the crosslinker, described further below, is in addition to the compound having a hydroxy functional alkyl polyurea compound and/or hydroxy functional alkyl polyurea moiety. If the $R_2$ group comprises a substituted or unsubstituted $C_1$ to $C_{36}$ alkyl group, the film-forming resin may contain COOH functionality. Such functionality may react with the crosslinker and/or the polyurea; reaction with the polyurea will result in an ester linkage.

The compositions of the present invention may comprise a polymer or oligomer comprising a repeat unit having a hydroxy functional alkyl polyurea of the formula:

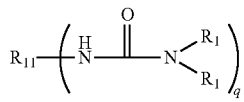

wherein $R_{11}$ is derived from a polymerizable moiety; wherein each $R_1$ is independently a hydrogen, an alkyl having at least 1 carbon, or a hydroxy functional alkyl having 2 or more carbons and at least one $R_1$ is a hydroxy functional alkyl having 2 or more carbons; and q is 1 or greater. Compositions comprising such a polymer or oligomer and applications therefor are also within the scope of the present invention.

$R_2$ may comprise an isocyanurate moiety, biuret moiety, allophonate moiety, glycoluril moiety, benzoguanamine moiety, polyetheramine moiety, and/or polymeric moiety different from a polyetheramine and having an Mn of 500 or greater. An isocyanurate will be understood as referring to a compound having three isocyanate groups, typically in ring form, and is sometimes referred to as a trimer. This can include compounds having one or more isocyanurate moieties. Isocyanurates can be purchased from COVESTRO and VENCORE X Chemical. Suitable commercially available isocyanurates include DESMODUR N 3300A, DESMODUR N3800, DESMODUR N3790, DESMODUR N3400, DESMODUR N3600, DESMODUR N3900, DESMODUR RC, VESTANAT T1890/100, EASAQUA WT 2102, EASAQUA X D 401, EASAQUA M 501, EASAQUA X D 803, EASAQUA M 502, EASAQUA X L 600. Unsaturated isocyanate monomers include but are not limited to 2-acryloyloxyethyisocyanate (AOI), 2-methacryloyloxyethyl isocyanate (MOI), alpha, alpha-dimethyl meta-isopropenyl benzyl isocyanate (TMI), and the adduct of 2-hydroxyethyl acrylate (HEA) and IPDI in 1:1 ratio. A particularly suitable hydroxy functional alkyl polyurea formed from an isocyanurate is shown below:

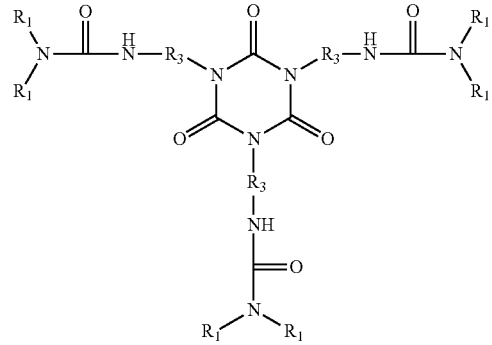

wherein $R_1$ is as described above and each $R_3$ independently comprises an alkyl, aryl, alkylaryl, arylalkyl, alicyclic, and/or polyetheralkyl group.

A particularly suitable hydroxy functional alkyl polyurea formed from a bis-isocyanurate is shown below:

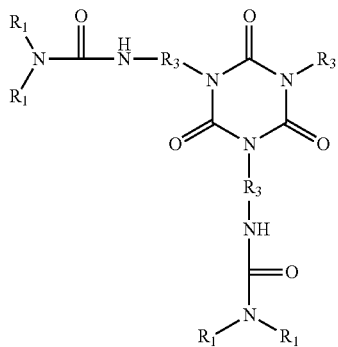 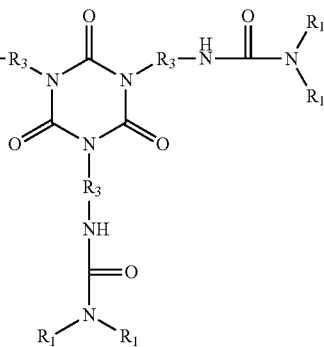

wherein $R_1$ and $R_3$ are as described above, and $R_4$ is a residue of polyamine.

A biuret will be understood as referring to a compound that results upon the condensation of two molecules of urea, and is sometimes referred to as a carbamylurea. Biurets are commercial available from VENCORE X Chemical and COVESTRO as, for example, DESMODUR N-75, DESMODUR N-100, and DESMODUR N-3200, HDB 75B, HDB 75M, HDB 75MX, HDB-LV. A particularly suitable hydroxy functional alkyl polyurea formed from a biuret is shown below:

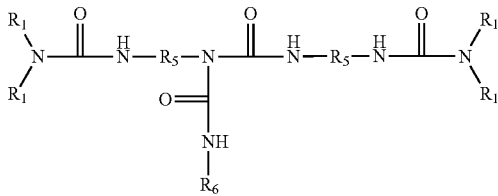

wherein $R_1$ is as described above, each $R_5$ independently comprises an alkyl, aryl, alkylaryl, arylalkyl, alicyclic, and/or polyetheralkyl group and $R_6$ comprises H or an alkyl group.

Uretidione is a dimer of diisocyanate, examples of which include DESMODUR N-3400 polyisocyanate, a blend of the trimer and uretidione of HDI. An example is shown below where $R_5$ is as described above:

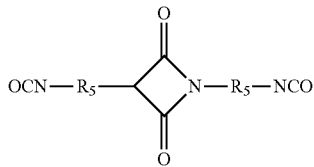

An allophonate will be understood as referring to a compound made from urethane and isocyanate. A method for making an allophonate is described at Surface Coating, Vol 1, Raw material and their usage, Landon New York, Chapman and Hall, Page 106. The reaction is generally depicted below where $R_5$ and $R_6$ are as described above and $R_7$ comprises the residue of a primary alcohol:

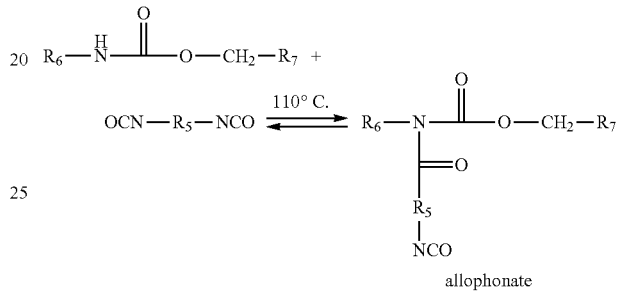

allophonate

A glycoluril will be understood as referring to a compound composed of two cyclic urea groups joined across the same two-carbon chain, a suitable example of which includes the below:

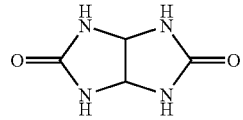

Glycoluril is widely commercially available, such as from Sigma-Aldrich. Glycoluril can react with diisocyanate in the equivalent ratio of 1:2 to form isocyanate functional glycoluril, and isocyanate functional glycoluril can further react with hydroxylamine to form hydroxy functional alkyl polyureas with glycoluril moiety.

Benzoguanamine is also known as 6-phenyl-1,3,5-triazine-2,4-diamine and is commercially available from The Chemical Company, Jamestown, R.I. Benzoguanamine can react with diisocyanate in the equivalent ratio of 1:2 to form isocyanate functional benzoguanamine, and isocyanate functional benzoguanamine can further react with hydroxylamine to form hydroxy functional alkyl polyureas with a benzoguanamine moiety.

A polyether amine will be understood as referring to a compound having one or more amine groups attached to a polyether backbone such as one characterized by propylene oxide, ethylene oxide, or mixed propylene oxide and ethylene oxide repeating units in their respective structures, such as, for example, one of the JEFFAMINE series products. Examples of such polyetheramines include aminated propoxylated pentaerythritols, such as JEFFAMINE XTJ-616, and those represented by Formulas (IV) through (VI).

According to Formula (IV) the polyether amine may comprise:

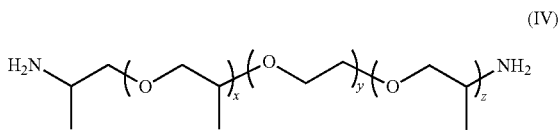

(IV)

wherein y=0-39, x+z=1-68.

Suitable amine-containing compounds represented by Formula (IV) include, but are not limited to, amine-terminated polyethylene glycol such as those commercially available from Huntsman Corporation in its JEFFAMINE ED series, such as JEFFAMINE HK-511, JEFFAMINE ED-600, JEFFAMINE ED-900 and JEFFAMINE ED-2003, and amine-terminated polypropylene glycol such as in its JEFFAMINE D series, such as JEFFAMINE D-230, JEFFAMINE D-400, JEFFAMINE D-2000 and JEFFAMINE D-4000.

According to Formula (V) the polyetheramine may comprise:

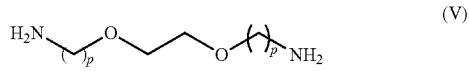

(V)

wherein each p independently is 2 or 3.

Suitable amine-containing compounds represented by Formula (V) include, but are not limited to, amine-terminated polyethylene glycol based diamines, such as Huntsman Corporation's JEFFAMINE EDR series, such as JEFFAMINE EDR-148 and JEFFAMINE EDR-176.

According to Formula (VI) the polyetheramine may comprise:

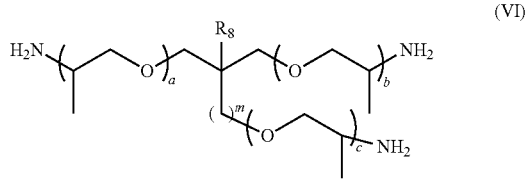

(VI)

wherein $R_8$ is H or $C_2H_5$, m=0 or 1, a+b+c=5-85.

Suitable amine-containing compounds represented by Formula (VI) include, but are not limited to, amine-terminated propoxylated trimethylolpropane or glycerol, such as Huntsman Corporation's JEFFAMINE T series, such as JEFFAMINE T-403, JEFFAMINE T-3000 and JEFFAMINE T-5000.

Particularly suitable are di- and tri-amines, such as 4,7,10-trioxa-1,13-tridecanediamine, JEFFAMINE D400, JEFFAMINE D4000, JEFFAMINE D2000 and JEFFAMINE T403.

Polyetheramine can react with diisocyanate in the equivalent ratio of 1:2 to form isocyanate functional polyetheramine, and isocyanate functional polyetheramine can further react with hydroxylamine to form hydroxy functional alkyl polyureas with a polyetheramine moiety.

A "polymeric moiety" as used herein in the context of R2 refers to any polymer or oligomer to which has been attached two to six hydroxy functional alkyl polyurea groups. The polymer can be, for example, a polyester polyurethane, a polyether polyurethane, or a polyamide polyurethane. The moiety can itself contain functionality, such as acid functionality, hydroxy functionality, and/or amine functionality. The polymeric moiety (which may be oligomeric as noted above) has an Mn of 500 or greater, such as 1000 or greater, 2500 or greater, 4000 or greater, or 5,000 or greater. Mn, as used herein, refers to the number average molecular weight and means the theoretical value as determined by Gel Permeation Chromatography using Waters 2695 separation module with a Waters 410 differential refractometer (RI detector) and polystyrene standards. The Mn values reported according to the invention were determined using this method. Tetrahydrofuran (THF) was used as the eluent at a flow rate of 1 ml min$^{-1}$, and two PL Gel Mixed C columns were used for separation.

In all cases, $R_2$ may be substituted or unsubstituted. When $R_2$ comprises a substituted or unsubstituted $C_1$ to $C_{36}$ alkyl group and/or an aromatic group, the alkyl group may have two to ten carbon atoms, such as six carbon atoms. The alkyl group may derive from an isocyanate, such as a diisocyanate. Suitable examples include isophorone diisocyanate and hexamethylene isocyanate. The aromatic group may derive from an aromatic ring containing isocyanate, suitable examples of which include methylene diphenyl diisocyanate, toluene diisocyanate and tetramethylxylylene diisocyanate.

$R_{11}$ can be derived from any compound that comprises a polymerizable moiety, and can be substituted or unsubstituted, branched or unbranched. A "polymerizable moiety" can include any moiety capable of undergoing polymerization with another monomer, polymer or oligomer. Upon this reaction, the hydroxy functional alkyl polyurea monomer will be polymerized into the backbone and/or at the terminus of a polymer. For example, $R_{11}$ may comprise an acrylic moiety and/or other reactive unsaturation, which could then be polymerized with other acrylic and/or unsaturated monomers, oligomers and/or polymers. Such acrylic/unsaturated moiety could also react with itself to form a homopolymer. The unsaturation could also be reacted with an unsaturated polyester, polyurethane, polyurea, polysiloxane, and the like. A polymerizable moiety can be introduced onto the hydroxy functional alkyl polyurea by, for example, reacting an isocyanate functional acrylate with the amine nitrogen on the urea. The polymerizable hydroxy functional alkyl polyurea can then be further reacted with one or more other monomers to form a polymer. The polymerizable hydroxy functional alkyl polyurea, or "repeat unit", can itself be described as a monomer or a pre-polymer, depending on molecular weight. Such a repeat unit, or the residue thereof, can further form a latex, such as a core-shell latex. Procedures for forming lattices, including core-shell lattices, are well known, and are also described in Example A in U.S. Pat. No. 8,846,156, which example is incorporated by reference herein. Polymers according to the present invention comprising the hydroxy functional alkyl polyurea in any form can exclude monomers having reacted or unreacted oxirane functionality, styrene, ethyl acrylate and/or acrylamide.

Certain hydroxy functional alkyl polyureas of, and/or used according to, the invention may be made by reacting an isocyanate-containing compound with amino alcohol. Any isocyanate-containing compound having at least two isocyanate groups can be used, such as any of those described above. It will be appreciated that the "$R_2$" and "$R_{11}$" group will reflect the isocyanate-containing compound selected, if one is used.

Similarly, any amino alcohol having two or more carbon atoms can be used, and the "$R_1$" group will reflect the amino alcohol selected. The amino alcohol can have one, two or more hydroxyl functional groups. One or more amino alcohols can be used, which will result in different $R_1$ groups being present on the polyurea. $R_1$ can also be hydrogen or an alkyl group. Suitable amino alcohols include monoethanol amine, diethanol amine and diisopropyl amine.

Generally, the hydroxyl functional alkyl polyureas can be made by reacting amino alcohol with an isocyanate-containing compound in an organic polar solvent, such as alcohol or water. The equivalent ratio of amine to isocyanate can be 2-1:1-2, such as 1:1.

The hydroxy functional alkyl polyureas of, and/or used according to, the invention may be made by alternative methods as well. For example, amino alcohols can react with carbonate to form hydroxylalkyl carbamate, and hydroxylalkyl carbamate can further react with amines to form hydroxy functional alkyl polyureas.

The number average molecular weight ("Mn") of the hydroxy functional alkyl polyurea (even when the polyurea is in the form of a monomer or prepolymer, but not when $R_2$ is a polymeric moiety) can be 100 or greater, such as 350 or greater, or 1,000 or greater, and/or can be 10,000 or lower, 6,000 or lower, 3,000 or lower, or 2,000 or lower. The Mn of the hydroxy functional alkyl polyurea when $R_2$ is a polymeric moiety can be greater than 500, such as 600 or greater, 750 or greater, 1000 or greater, 5,000 or greater, or 10,000 or greater.

The present invention, as noted above, includes a composition comprising a film-forming resin, a crosslinker, and any of the hydroxy functional alkyl polyureas, monomers, oligomers, pre-polymers or polymers described above. The composition can be, for example, a coating, an adhesive or a sealant. It will be appreciated that coatings, sealants and adhesives often comprise similar components but are formulated differently depending on the needs of the user. The hydroxy functional alkyl polyurea may itself form all or part of the film-forming resin. That is, the polyurea can itself be film-forming. "Film-forming" means that the composition, upon drying and/or curing, can form a continuous film on a surface.

Any film-forming resin and crosslinker can be used according to the present invention. It may be desired to choose film-forming resins and functionalities that are not negatively affected by the hydroxy functional alkyl polyurea additive. The film-forming resin can be selected from, for example, acrylic polymers, polyester polymers, polyurethane polymers, polyamide polymers, polyether polymers, polysiloxane polymers, PVC polymers, PVDF polymers, Nylon polymers, copolymers thereof, and mixtures thereof. Generally, these polymers can be any polymers of these types made by any method known to those skilled in the art. Such polymers may be solid, solvent-borne or water-dispersible, emulsifiable, or of limited water solubility. The functional groups on the film-forming resin may be selected from any of a variety of reactive functional groups including, for example, carboxylic acid groups, amine groups, epoxide groups, hydroxyl groups, thiol groups, carbamate groups, amide groups, urea groups, isocyanate groups (including blocked isocyanate groups) mercaptan groups, and combinations thereof. The film-forming resin can comprise an acid functional polyester resin and/or an acid functional acrylic resin. One skilled in the art can select an appropriate crosslinker based on this functionality from known crosslinkers such as melamine, phenolic, carbodiimide, hydroxyalkylamide, isocyanate, blocked isocyanate, benzaguanamine, triglycidyl isocyanurate ("TGIC"), epoxies, oxazolines, and the like. Appropriate mixtures of film-forming resins may also be used in the preparation of the present compositions, as can mixtures of crosslinkers. A particularly suitable film-forming resin may be a polyolefin, such as an acid functional polyolefin, a suitable example of which is an ethylene acrylic acid copolymer commercially available from Dow as PRIMACOR 5890I, or the polyolefin can be in dispersion form, such as is taught in United States Patent Application Publication Number 2016/0280951 A1 at paragraph 5 or those prepared as described in WO Number 2013/191825 A1, page 14, line 16 through page 15, line 23 and in the examples.

The composition can comprise, for example, 10 weight percent or greater of film-forming resin, such as 50 weight percent or greater or 75 weight percent or greater and/or can comprise 99 weight percent or lower of film-forming resin, such as 80 weight percent or lower or 70 weight percent or lower, with weight percent based on total solid weight of the composition. The composition can comprise, for example, 1 weight percent or greater crosslinker, such as 3 weight percent or greater or 5 weight percent or greater and/or can comprise 50 weight percent or lower of crosslinker, such as 30 weight percent or lower or 10 weight percent or lower, with weight percent based on total solid weight of the composition. The composition can comprise, for example, 0.5 weight percent or greater of hydroxy functional alkyl polyurea, such as 2 weight percent or greater or 7 weight percent or greater, and/or can comprise 50 weight percent or lower hydroxy functional alkyl polyurea, such as 30 weight percent or lower, 10 weight percent or lower, 8 weight percent or lower or 5 weight percent or lower, with weight percent based on total solid weight of the composition. A particularly suitable amount of polyurea is 0.5 to 5.0 weight percent based on total solid weight of the composition.

As noted above, it is also possible that the hydroxy functional alkyl polyurea is itself part or all of the film-forming resin. For example, the hydroxy functional alkyl polyurea monomer(s) and/or pre-polymer(s) described above may be incorporated into a polymer that serves as the film-forming resin, or may be a polymer that itself is a film-forming resin. Such resin could react with an appropriately selected crosslinker. The crosslinker could be selected from any crosslinker known in the art to crosslink with the functionality on the polymer. The polymer could also be self-crosslinking. That is, the only reactive component of the composition may be the hydroxy functional alkyl polyurea described herein. The polymer, and crosslinker therefor if used, can form all of the film-forming resin, or can be used with any other film-forming resin(s) and optionally crosslinker(s) therefor, such as those described above. When a film-forming resin and crosslinker therefor is used in addition to the hydroxy functional alkyl polyurea polymer, the crosslinker may be the same or different as the crosslinker used for the polymer.

The compositions of the present invention may comprise more than one of any of the compounds having a hydroxy functional alkyl polyurea and/or hydroxy functional alkyl polyurea moiety described herein. For example, a composition might comprise both a hydroxyl functional alkyl polyurea with an $R_{11}$ group is derived from a polymerizable moiety and with an $R_2$ group in which $R_2$ is a polymeric moiety having an Mn of 500 or greater. A particularly suitable such composition is one in which the $R_{11}$ comprises an acrylate functionality and the $R_2$ group comprises an acid functional polyurethane, such as a polyester or polyether polyurethane.

The composition may comprise one or more solvents including water or organic solvents. Suitable organic solvents include glycols, glycol ether alcohols, alcohols, ketones, and aromatics, such as xylene and toluene, acetates, mineral spirits, naphthas and/or mixtures thereof. "Acetates" include the glycol ether acetates. The solvent can be a non-aqueous solvent. "Non-aqueous solvent" and like terms means that less than 50% of the solvent is water. For example, less than 10%, or even less than 5% or 2%, of the solvent can be water. It will be understood that mixtures of solvents, including or excluding water in an amount of less than 50%, can constitute a "non-aqueous solvent". The composition may be aqueous or water-based. This means that 50% or more of the solvent is water. These embodiments have less than 50%, such as less than 20%, less than 10%, less than 5% or less than 2% solvent or essentially solvent free.

The composition may be in solid particulate form, i.e. a powder coating. Such coatings will be appreciated as being environmentally friendly, as only water is released on cure.

The compositions of the present invention may further comprise a catalyst. Any catalyst typically used to catalyze crosslinking between a hydroxyl group and an acid or isocyanate may be used. Examples of such a catalyst include those having metal complexes with metals such as zinc, zirconium, titanium and tin and other Lewis acids. Amines, including guanamines, may also be used. The use of a catalyst, it will be appreciated, causes the cure of the coating to occur faster. Notably, catalysts are not effective at speeding the cure of beta-hydroxyl alkyl amides with the film-forming resins listed above. Accordingly, it was a surprising result that catalysts promoted cure in the present coatings.

If desired, the compositions can comprise other optional materials well known in the art of formulating, such as colorants, plasticizers, abrasion resistant particles, anti-oxidants, hindered amine light stabilizers, UV light absorbers and stabilizers, surfactants, flow control agents, thixotropic agents, fillers, organic cosolvents, reactive diluents, catalysts, grind vehicles, slip agents, moisture scavenger and other customary auxiliaries.

As used herein, the term "colorant" means any substance that imparts color and/or other opacity and/or other visual effect, e.g. gloss, to the composition. The colorant can be added to the coating in any suitable form, such as discrete particles, dispersions, solutions and/or flakes. A single colorant or a mixture of two or more colorants can be used in the coatings of the present invention. Particularly suitable for packaging coatings are those approved for food contact, such as titanium dioxide; iron oxides, such as black iron oxide; aluminum paste; aluminum powder such as aluminum flake; carbon black; ultramarine blue; phthalocyanines, such as phthalocyanine blue and phthalocyanine green; chromium oxides, such as chromium green oxide; graphite fibrils; ferried yellow; quindo red; and combinations thereof, and those listed in Article 178.3297 of the Code of Federal Regulations, which is incorporated by reference herein.

Example colorants include matting pigments, dyes and tints, such as those used in the paint industry and/or listed in the Dry Color Manufacturers Association (DCMA), as well as special effect compositions. A colorant may include, for example, a finely divided solid powder that is insoluble but wettable under the conditions of use. A colorant can be organic or inorganic and can be agglomerated or non-agglomerated. Colorants can be incorporated into the coatings by grinding or simple mixing. Colorants can be incorporated by grinding into the coating by use of a grind vehicle, such as an acrylic grind vehicle, the use of which will be familiar to one skilled in the art.

Example pigments and/or pigment compositions include, but are not limited to, carbazole dioxazine crude pigment, azo, monoazo, disazo, naphthol AS, salt type (lakes), benzimidazolone, condensation, metal complex, isoindolinone, isoindoline and polycyclic phthalocyanine, quinacridone, perylene, perinone, diketopyrrolo pyrrole, thioindigo, anthraquinone, indanthrone, anthrapyrimidine, flavanthrone, pyranthrone, anthanthrone, dioxazine, triarylcarbonium, quinophthalone pigments, diketo pyrrolo pyrrole red ("DPPBO red"), titanium dioxide, carbon black, carbon fiber, graphite, other conductive pigments and/or fillers and mixtures thereof. The terms "pigment" and "colored filler" can be used interchangeably.

Example dyes include, but are not limited to, those that are solvent and/or aqueous-based such as acid dyes, azoic dyes, basic dyes, direct dyes, disperse dyes, reactive dyes, solvent dyes, sulfur dyes, mordant dyes, for example, bismuth vanadate, anthraquinone, perylene aluminum, quinacridone, thiazole, thiazine, azo, indigoid, nitro, nitroso, oxazine, phthalocyanine, quinoline, stilbene, and triphenyl methane.

Example tints include, but are not limited to, pigments dispersed in water-based or water-miscible carriers such as AQUA-CHEM 896 commercially available from Degussa, Inc., CHARISMA COLORANTS and MAXITONER INDUSTRIAL COLORANTS commercially available from Accurate Dispersions division of Eastman Chemicals, Inc.

As noted above, the colorant can be in the form of a dispersion including, but not limited to, a nanoparticle dispersion. Nanoparticle dispersions can include one or more highly dispersed nanoparticle colorants and/or colorant particles that produce a desired visible color and/or opacity and/or visual effect. Nanoparticle dispersions can include colorants such as pigments or dyes having a particle size of less than 150 nm, such as less than 70 nm, or less than 30 nm. Nanoparticles can be produced by milling stock organic or inorganic pigments with grinding media having a particle size of less than 0.5 mm. Example nanoparticle dispersions and methods for making them are identified in U.S. Pat. No. 6,875,800 B2, which is incorporated herein by reference. Nanoparticle dispersions can also be produced by crystallization, precipitation, gas phase condensation, and chemical attrition (i.e., partial dissolution). In order to minimize re-agglomeration of nanoparticles within the coating, a dispersion of resin-coated nanoparticles can be used. As used herein, a "dispersion of resin-coated nanoparticles" refers to a continuous phase in which is dispersed discreet "composite microparticles" that comprise a nanoparticle and a resin coating on the nanoparticle. Example dispersions of resin-coated nanoparticles and methods for making them are described, for example, in U.S. Pat. No. 7,605,194 at column 3, line 56 to column 16, line 25, the cited portion of which being incorporated herein by reference.

Example special effect compositions that may be used include pigments and/or compositions that produce one or more appearance effects such as reflectance, pearlescence, metallic sheen, phosphorescence, fluorescence, photochromism, photosensitivity, thermochromism, goniochromism and/or color-change. Additional special effect compositions can provide other perceptible properties, such as opacity or texture. For example, special effect compositions can produce a color shift, such that the color of the coating changes when the coating is viewed at different angles. Example color effect compositions are identified in U.S. Pat. No. 6,894,086, incorporated herein by reference. Additional color effect compositions can include transparent coated mica and/or synthetic mica, coated silica, coated alumina, a transparent liquid crystal pigment, a liquid crystal coating, and/or any composition wherein interference results from a refractive index differential within the material and not because of the refractive index differential between the surface of the material and the air.

A photosensitive composition and/or photochromic composition, which reversibly alters its color when exposed to one or more light sources, can be used in the coating of the present invention. Photochromic and/or photosensitive compositions can be activated by exposure to radiation of a specified wavelength. When the composition becomes excited, the molecular structure is changed and the altered structure exhibits a new color that is different from the original color of the composition. When the exposure to radiation is removed, the photochromic and/or photosensitive composition can return to a state of rest, in which the original color of the composition returns. For example, the photochromic and/or photosensitive composition can be colorless in a non-excited state and exhibit a color in an excited state. Full color-change can appear within milliseconds to several minutes, such as from 20 seconds to 60 seconds. Example photochromic and/or photosensitive compositions include photochromic dyes.

The photosensitive composition and/or photochromic composition can be associated with and/or at least partially bound to, such as by covalent bonding, a polymer and/or polymeric materials of a polymerizable component. In contrast to some coatings in which the photosensitive composition may migrate out of the coating and crystallize into the substrate, the photosensitive composition and/or photochromic composition associated with and/or at least partially bound to a polymer and/or polymerizable component in accordance with the present invention, have minimal migration out of the coating. Example photosensitive compositions and/or photochromic compositions and methods for making them are identified in U.S. Pat. No. 8,153,344, and incorporated herein by reference.

In general, the colorant can be present in any amount sufficient to impart the desired visual and/or color effect. The colorant may comprise from 1 to 65 weight percent of the present compositions, such as from 3 to 40 weight percent or 5 to 35 weight percent, with weight percent based on the total weight of the compositions.

An "abrasion resistant particle" is one that, when used in a coating, will impart some level of abrasion resistance to the coating as compared with the same coating lacking the particles. Suitable abrasion resistant particles include organic and/or inorganic particles. Examples of suitable organic particles include but are not limited to diamond particles, such as diamond dust particles, and particles formed from carbide materials; examples of carbide particles include but are not limited to titanium carbide, silicon carbide and boron carbide. Examples of suitable inorganic particles include, but are not limited to silica; alumina; alumina silicate; silica alumina; alkali aluminosilicate; borosilicate glass; nitrides including boron nitride and silicon nitride; oxides including titanium dioxide and zinc oxide; quartz; nepheline syenite; zircon such as in the form of zirconium oxide; buddeluyite; and eudialyte. Particles of any size can be used, as can mixtures of different particles and/or different sized particles. For example, the particles can be microparticles, having an average particle size of 0.1 to 50, 0.1 to 20, 1 to 12, 1 to 10, or 3 to 6 microns, or any combination within any of these ranges. The particles can be nanoparticles, having an average particle size of less than 0.1 micron, such as 0.8 to 500, 10 to 100, or 100 to 500 nanometers, or any combination within these ranges.

Any slip agent can be used according to the present invention such as those commercial available from BYK Chemie or Dow Corning. A wax can also be used such as polyolefin wax, carnuba wax, polytetrafluoroethylene ("PTFE"), Fischer Tropsch wax, silicone or paraffin.

The hydroxy functional alkyl polyureas, and/or the compositions of the present invention, may be substantially free, may be essentially free and/or may be completely free of bisphenol A and epoxy compounds derived from bisphenol A ("BPA"), such as bisphenol A diglycidyl ether ("BADGE"). Such compounds are sometimes referred to as "BPA non intent" because BPA, including derivatives or residues thereof, are not intentionally added but may be present in trace amounts because of impurities or unavoidable contamination from the environment. The hydroxy functional alkyl polyureas and/or coatings can also be substantially free and may be essentially free and/or may be completely free of bisphenol F and epoxy compounds derivatived from bisphenol F, such as bisphenol F diglycidyl ether ("BFDGE"). The term "substantially free" as used in this context means the polyureas and/or coatings contain less than 1000 parts per million (ppm), "essentially free" means less than 100 ppm and "completely free" means less than 20 parts per billion (ppb) of any of the above mentioned compounds, derivatives or residues thereof.

In addition, the hydroxy functional alkyl polyureas and/or the compositions of the present invention may be substantially free, may be essentially free and/or may be completely free of formaldehyde and/or phenolic crosslinker, such as phenolic resin. The term "substantially free" as used in this context means the and/or coatings contain less than 1000 parts per million (ppm), "essentially free" means less than 100 ppm and "completely free" means less than 100 parts per billion (ppb) of formaldehyde compounds, derivatives or residues thereof. Such compositions do not substantially, essentially or completely release formaldehyde upon cure.

The present compositions can be applied to any substrates known in the art, for example, automotive substrates, marine substrates, industrial substrates, heavy duty equipment, packaging substrates, lumber, wood flooring and furniture, apparel, electronics including housings and circuit boards and including consumer electronics such as housings for computers, notebooks, smartphones, tablets, televisions, gaming equipment, computer equipment, computer accessories, MP3 players, and the like, glass and transparencies, sports equipment including golf balls, and the like. These substrates can be, for example, metallic or non-metallic. Metallic substrates include tin, steel, tin-plated steel, chromium passivated steel, galvanized steel, aluminum, and aluminum foil. Metal sheet as used herein refers to flat metal sheet and coiled metal sheet, which is coiled, uncoiled for coating and then re-coiled for shipment to a manufacturer. Non-metallic substrates include polymeric, plastic, polyester, polyolefin, polyamide, cellulosic, polystyrene, polyacrylic, poly(ethylene naphthalate), polypropylene, polyethylene, nylon, EVOH, polylactic acid, other "green" polymeric substrates, poly(ethyleneterephthalate) ("PET"), polycarbonate, polycarbonate acrylobutadiene styrene ("PC/ABS"), polyamide, wood, veneer, wood composite, particle board, medium density fiberboard, cement, stone, glass, paper, cardboard, textiles, leather both synthetic and natural, and the like. The substrate can be one that has been already treated in some manner, such as to impart visual and/or color effect. Suitable substrates can include those in which powder coatings are typically applied.

The compositions of the present invention can be applied by any means standard in the art, such as electrocoating, spraying, electrostatic spraying, dipping, rolling, brushing, and the like.

The compositions can be applied to a dry film thickness of 0.04 mils to 40 mils, such as 0.3 to 2 or 0.7 to 1.3 mils. The compositions can also be applied to a dry film thickness of 0.1 mils or greater, 0.5 mils or greater 1.0 mils or greater, 2.0 mils or greater, 5.0 mils or greater, or even thicker. In some applications, a dry film thickness of 1-20 microns, such as 2-6 microns, is desired. In some applications, a dry film thickness of 10-100 microns, such as 50-77 microns, might be desired. In other applications, such as when powder coatings are used, a dry film thickness of 0.5 to 50 mils, such as 1.5 to 8 mils or 2 to 4 mils, might be desired.

The compositions of the present invention can be used alone, or in combination with one or more other compositions, such as a coating system having two or more layers. For example, the compositions of the present invention can comprise a colorant or not and can be used as a primer, basecoat, and/or top coat. A "primer" will be understood as an undercoat or a coating typically applied to a surface prior to the decorative coating. For substrates coated with multiple coatings, one or more of those coatings can be coatings as described herein. The present coatings can also be used as a packaging "size" coating, wash coat, spray coat, end coat, and the like.

It will be appreciated that the compositions described herein can be either one component ("1K"), or multi-component compositions such as two component ("2K") or more. A 1K composition will be understood as referring to a composition wherein all the coating components are maintained in the same container after manufacture, during storage, etc. A 1K composition can be applied to a substrate and cured by any conventional means, such as by heating, forced air, and the like. The present compositions can also be multi-component, which will be understood as compositions in which various components are maintained separately until just prior to application. As noted above, the present compositions can be thermoplastic or thermosetting.

The composition can be a clearcoat. A clearcoat will be understood as a coating that is substantially transparent or translucent. A clearcoat can therefore have some degree of color, provided it does not make the clearcoat opaque or otherwise affect, to any significant degree, the ability to see the underlying substrate. The clearcoats of the present invention can be used, for example, in conjunction with a pigmented basecoat. The clearcoat can be formulated as is known in the coatings art.

The composition may also comprise a colorant, such as a pigmented basecoat used in conjunction with a clearcoat, or as a monocoat. A monocoat may be pigmented and used without a clearcoat on top. A particularly suitable use of the present compositions is as a pigmented monocoat, where the R is an acid functional polymer, with optional hydroxy functionality, having an Mn of 10,000 to 50,000. Another particularly suitable use of the present compositions is as a pigmented, two coat system where the first coat is not cured prior to application of the second coat; the two coats can then be cured together (and additional coats could also be applied both before and after cure). Such procedure is often referred to as a "wet-on-wet" process when the coatings are liquid, and "dust-on-dust" when the coatings are powder. The compositions of the present invention can be in one or both of the layers in the two coat system. Mixtures of compositions of the present invention are not limited to this application, and can be used according to any aspect of the invention.

Coatings as described herein are used in various industries to impart a decorative and/or protective finish. For example, such a coating or coating system may be applied to a vehicle. "Vehicle" is used herein in its broadest sense and includes all types of vehicles, such as but not limited to cars, trucks, buses, tractors, harvesters, other farm equipment, vans, golf carts, motorcycles, bicycles, railroad cars, airplanes, helicopters, boats of all sizes and the like. It will be appreciated that the portion of the vehicle that is coated according to the present invention may vary depending on why the coating is being used. For example, anti-chip primers may be applied to some of the portions of the vehicle as described above. When used as a colored basecoat or monocoat, the present coatings will typically be applied to those portions of the vehicle that are visible such as the roof, hood, doors trunk lid and the like, but may also be applied to other areas such as inside the trunk, inside the door and the like especially when the compositions are formulated as sealants or adhesives; for example, the compositions can be formulated so as to have a viscosity of 80,000 cps to 120,000 cps as measured by a Brookfield viscometer using spindle number 7 at 20 rpm speed, and applied to the floor pan of the passenger compartment, deck lid and roof with, for example, a 2-4 mm film thickness to provide sound and/or vibration damping to a vehicle (a "sound damping composition"). The present compositions can also be applied to those portions of the vehicle that are in contact with the driver and/or passengers, such as the steering wheel, dashboard, gear shift, controls, door handle and the like. Clearcoats will typically be applied to the exterior of a vehicle.

The compositions of the present invention can also be used in the manufacture of wood products, such as particle board or fiber board, such as MDF fiber board. For example, a composition comprising a compound having a hydroxy functional alkyl polyurea and/or a hydroxy functional alkyl polyurea moiety according to the present invention can be used in a composition with a resin, such as an acrylic latex. The composition can be further mixed with particulate wood such as saw dust and/or wood fiber ("wood particles"), and the mixture pressed between hot plates to form the product. Such formation processes are standard in the art, and the appropriate temperatures, pressures, and formulating parameters will be ascertainable by one skilled in the art. Accordingly, the present invention is further directed to a substrate formed with the above hydroxy functional alkyl polyurea composition of the present invention and wood particles. "Formed with" in this context means that the composition comprising a compound having a hydroxy functional alkyl polyurea and/or a hydroxy functional alkyl polyurea moiety serves as one of the building blocks of the substrate itself, as opposed to forming a coating on the substrate.

The compositions of the present invention are also suitable for use as packaging coatings. The application of various pretreatments and coatings to packaging is well established. Such treatments and/or coatings, for example, can be used in the case of metal cans, wherein the treatment and/or coating is used to retard or inhibit corrosion, provide a decorative coating, provide ease of handling during the manufacturing process, and the like. Coatings can be applied to the interior of such cans to prevent the contents from contacting the metal of the container. Contact between the metal and a food or beverage, for example, can lead to corrosion of a metal container, which can then contaminate the food or beverage. This is particularly true when the contents of the can are acidic in nature. The coatings applied to the interior of metal cans also help prevent corrosion in the headspace of the cans, which is the area between the fill line of the product and the can lid; corrosion in the headspace is particularly problematic with food products having a high salt content. Coatings can also be applied to the exterior of metal cans. Certain coatings of the present invention are particularly applicable for use with coiled metal stock, such as the coiled metal stock from which the ends of cans are made ("can end stock"), and end caps and closures are made ("cap/closure stock"). Since coatings designed for use on can end stock and cap/closure stock are typically applied prior to the piece being cut and stamped out of the coiled metal stock, they are typically flexible and extensible. For example, such stock is typically coated on both sides. Thereafter, the coated metal stock is punched. For can ends, the metal is then scored for the "pop-top" opening and the pop-top ring is then attached with a pin that is separately fabricated. The end is then attached to the can body by an edge rolling process. A similar procedure is done for "easy open" can ends. For easy open can ends, a score substantially around the perimeter of the lid allows for easy opening or removing of the lid from the can, typically by means of a pull tab. For caps and closures, the cap/closure stock is typically coated, such as by roll coating, and the cap or closure stamped out of the stock; it is possible, however, to coat the cap/closure after formation. Coatings for cans subjected to relatively stringent temperature and/or pressure requirements should also be resistant to popping, corrosion, blushing and/or blistering.

Accordingly, the present invention is further directed to a package coated at least in part with any of the coating compositions described above. A "package" is anything used to contain another item, particularly for shipping from a point of manufacture to a consumer, and for subsequent storage by a consumer. A package will be therefore understood as something that is sealed so as to keep its contents free from deterioration until opened by a consumer. The manufacturer will often identify the length of time during which the food or beverage will be free from spoilage, which typically ranges from several months to years. Thus, the present "package" is distinguished from a storage container or bakeware in which a consumer might make and/or store food; such a container would only maintain the freshness or integrity of the food item for a relatively short period. A package according to the present invention can be made of metal or non-metal, for example, plastic or laminate, and be in any form. An example of a suitable package is a laminate tube. Another example of a suitable package is a metal can. The term "metal can" includes any type of metal can, container or any type of receptacle or portion thereof that is sealed by the food/beverage manufacturer to minimize or eliminate spoilage of the contents until such package is opened by the consumer. One example of a metal can is a food can; the term "food can(s)" is used herein to refer to cans, containers or any type of receptacle or portion thereof used to hold any type of food and/or beverage. "Beverage can" may also be used to refer more specifically to a food can in which a beverage is packaged. The term "metal can(s)" specifically includes food cans (including beverage cans) and also specifically includes "can ends" including "E-Z open ends", which are typically stamped from can end stock and used in conjunction with the packaging of food and beverages. The term "metal cans" also specifically includes metal caps and/or closures such as bottle caps, screw top caps and lids of any size, lug caps, and the like. The metal cans can be used to hold other items as well, including, but not limited to, personal care products, bug spray, spray paint, and any other compound suitable for packaging in an aerosol can. The cans can include "two piece cans" and "three-piece cans" as well as drawn and ironed one-piece cans; such one piece cans often find application with aerosol products. Packages coated according to the present invention can also include plastic bottles, plastic tubes, laminates and flexible packaging, such as those made from PE, PP, PET and the like. Such packaging could hold, for example, food, toothpaste, personal care products and the like.

The coating can be applied to the interior and/or the exterior of the package. For example, the coating can be rollcoated onto metal used to make a three-piece metal can, can end stock and/or cap/closure stock, or sprayed, flow coated or gravure or roll coated onto a formed two piece metal can. The coating is applied to a coil or sheet by roll coating; the coating is then cured by radiation and can ends are stamped out and fabricated into the finished product, i.e. can ends. The coating could also be applied as a rim coat to the bottom of the can; such application can be by roll coating. The rim coat functions to reduce friction for improved handling and protection during the continued fabrication and/or processing of the can. The coating can also be applied to caps and/or closures; such application can include, for example, a protective varnish that is applied before and/or after formation of the cap/closure and/or a pigmented enamel post applied to the cap, particularly those having a scored seam at the bottom of the cap. Decorated can stock can also be partially coated externally with the coating described herein, and the decorated, coated can stock used to form various metal cans.

Metal coils, having wide application in many industries, are also substrates that can be coated according to the present invention. Coil coatings also typically comprise a colorant. Metal parts can also be coated according to the present invention. A metal part is a substrate made all or in part from metal that has been formed into a desired shape. Any of the substrates described herein can have sharp edges. "Sharp edge(s)" can refer to edges that have been stamped, sheared, machine cut, laser cut and the like.

The compositions of the present invention are also suitable for use as heavy duty equipment and/or general industrial powder coatings, either as monocoats or multicoat systems, such as two coat systems. The application of various pretreatments and coatings to heavy duty equipment or general industrial substrates is well established. Such treatments and/or coatings, for example, can be used in the case wherein the treatment and/or coating is used to retard or inhibit corrosion, provide a decorative coating, provide ease of handling during the manufacturing process, protect sharp edges and the like. The compositions of the present invention can provide electrostatic control for powder coatings, which provides additional coating protection to sharp edges that are points of corrosion failure in the field.

After application to the substrate, the coating composition may be cured by any appropriate means, for cure times and temperatures appropriate for the chemistry of the composition, the substrate being coated, and the like. In some applications a relatively low cure temperature for a relatively long time may be desired, such as a cure temperature of 140° C. to 100° C. for 60 minutes or less, such as 20 or 30 minutes. In other applications a relatively high cure temperature for a relatively short time may be desired, such as a cure temperature of 300° C. to 200° C. for a time of three minutes or less, such as two minutes or less, or one minute or less, or 30 seconds or less or 15 seconds or less. Accordingly, the present coatings can be used across a broad range of industries and cure conditions. Depending on the cure temperature, time, the type of film former used and the like, the hydroxy functional alkyl polyurea and/or hydroxy functional alkyl polyurea moiety may actually react with the film-forming resin. If such a reaction between the film former and the polyurea occurs, it will not be the only mechanism of cure for the composition when another crosslinker is used.

In addition to their use in compositions and substrates as described above, any of the polyurea compounds as described herein can be used in thermoplastic acid functional polymers such as polyesters, ethylene acrylic acid copolymers and terpolmers, and ionomers. In melt blends with thermoplastic polymers, the polyurea compounds can serve as additives, cross-linkers, chain extenders, to increase the hydrolysis resistance of polyesters, and to modify viscosity for applications such as extruded fibers, films, injection molded articles, extrusion coating, blow molding, extrusion blowmolding, and extrusion. For example, the polyurea compounds can be added to thermoplastic compositions such as nylon, pvdf compositions, polyesters, polyolefins, PVC, PVA, acrylic and the like. The hydroxy functional alkyl polyureas described herein can also be used in applications currently employing carbodiimide additives.

As used herein, unless otherwise expressly specified, all numbers such as those expressing values, ranges, amounts or percentages may be read as if prefaced by the word "about", even if the term does not expressly appear. Also, any numerical range recited herein is intended to include all sub-ranges subsumed therein. Singular encompasses plural and vice versa. For example, although reference is made herein to "a" composition comprising "a" compound having "a" hydroxy functional alkyl polyurea moiety, "a" film-forming resin, "a" crosslinker, "an" isocyanate, "an" alkanol amine, "a" crosslinker, "the" residue of "an", and the like, one or more of each of these and any other components can be used. As used herein, the term "polymer" refers to oligomers and both homopolymers and copolymers, and the prefix "poly" refers to two or more. Including, for example and like terms means including for example but not limited to. When ranges are given, any endpoints of those ranges and/or numbers within those ranges can be combined within the scope of the present invention. The word "comprising" and forms of the word "comprising", as used in this description and in the claims, does not limit the present invention to exclude any variants or additions. Additionally, although the present invention has been described in terms of "comprising", the processes, materials, and coating compositions detailed herein may also be described as "consisting essentially of" or "consisting of".

Non-limiting aspects of the invention include:
1. A composition comprising a compound having a hydroxy functional alkyl polyurea compound and/or hydroxy functional alkyl polyurea moiety having the formula:

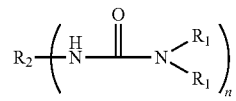

wherein $R_2$ comprises a substituted or unsubstituted $C_1$ to $C_{36}$ alkyl group, an aromatic group, an isocyanurate moiety, biuret moiety, allophonate moiety, glycoluril moiety, benzoguanamine moiety, polyetheramine moiety, and/or polymeric moiety different from a polyetheramine and having an Mn of 500 or greater; wherein each $R_1$ is independently a hydrogen, alkyl having at least 1 carbon, or a hydroxy functional alkyl having 2 or more carbons and at least one $R_1$ is a hydroxy functional alkyl having 2 or more carbons; and n is 2-6, and wherein the polyurea is present in the composition in an amount of 0.5 to 10 weight percent based on total solid weight.

2. A composition comprising a polymer or oligomer comprising a repeat unit having a hydroxyl functional alkyl polyurea of the formula:

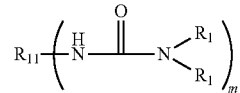

wherein $R_{11}$ is derived from a polymerizable moiety; wherein each $R_1$ is independently a hydrogen, an alkyl having at least 1 carbon, or a hydroxy functional alkyl having 2 or more carbons and at least one $R_1$ is a hydroxy functional alkyl having 2 or more carbons; and q is 1 or greater.

3. A composition comprising a film-forming resin, a crosslinker, and a compound having a hydroxy functional alkyl polyurea and/or hydroxy functional alkyl polyurea moiety having the formula

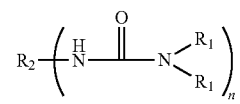

wherein $R_2$ comprises a substituted or unsubstituted $C_1$ to $C_{36}$ alkyl group, an aromatic group, an isocyanurate moiety, biuret moiety, allophonate moiety, glycoluril moiety, benzoguanamine moiety, polyetheramine moiety, and/or polymeric moiety different from a polyetheramine and having an Mn of 500 or greater; wherein each $R_1$ is independently a hydrogen, alkyl having at least 1 carbon, or a hydroxy functional alkyl having 2 or more carbons and at least one $R_1$ is a hydroxy functional alkyl having 2 or more carbons; and n is 2-6.

4. The composition of aspect 1 or 3, wherein $R_2$ comprises an isocyanate moiety.

5. The composition of any preceding aspect, wherein at least one $R_1$ comprises a 2-hydroxyethyl or 2-hydroxypropyl group.

6. The composition of aspect 3, wherein the film-forming resin comprises an acid functional polyester resin and the crosslinker comprises hydroxyl alkyl amide.

7. The composition of any aspect 1 or 3 to 6, wherein $R_2$ comprises a substituted or unsubstituted $C_2$-$C_{12}$, such as a substituted or unsubstituted $C_6$.

8. The composition of any aspect 1 or 3 to 7, wherein $R_2$ comprises a polymeric moiety having an Mn of 500 or greater, such as acid functional polyurethane.

9. The composition of any preceding aspect, wherein the composition is substantially, essentially and/or completely free of BPA.

10. The composition of any preceding aspect, wherein the coating is substantially, essentially or completely formaldehyde free and does not substantially, essentially or completely release formaldehyde upon curing.

11. The composition of any preceding aspect, wherein the composition is formulated as a coating.

12. The composition of any preceding aspect, wherein the composition is a powder coating.

13. The composition of any preceding aspect, wherein the composition is a powder coating primer.

14. The composition of any preceding aspect, wherein the composition is a powder coating monocoat.
15. The composition of any preceding aspect, further comprising a catalyst.
16. The composition of aspect 16, wherein the catalyst comprises tin and/or titanium.
17. The composition of any preceding aspect, wherein the $R_1$ groups do not contain an ether linkage.
18. The composition of any preceding aspect, comprising 2 or more different hydroxy functional alkyl polyureas.
19. A substrate coated at least in part with the composition of any preceding aspect.
20. The substrate of aspect 19, wherein the substrate is selected from a package, a metal can, a metal part, and a vehicle or has sharp edges.
21. The substrate of aspect 19, wherein the substrate comprises rubber or plastic or a metal sheet or coil.
22. The composition of any of aspects 3 to 18, wherein the film-forming resin comprises polyurethane, an acrylic latex, such as one having an acid value of 10 to 15 mg KOH/g, or such as 10 mg KOH/g or greater; a polyurethane acrylic latex; an acrylic resin; a polyester resin; an epoxy resin; and/or a polyolefin, such as a polyolefin dispersion.
23. A substrate formed with a hydroxy functional alkyl polyurea of any preceding aspect.
24. The substrate of aspect 23, wherein the substrate is a wood product, such as particle board or fiber board.
25. The composition of any preceding aspect, wherein the composition is formulated as a sound damping composition.

EXAMPLES

The following examples are intended to illustrate the invention and should not be construed as limiting the invention in any way.

Example 1

Synthesis of 1,1,6,6-hexamethylene-3,3,3',3'-tetrakis (2-hydroxyethyl)-bis-urea 315.4 g diethanolamine and 473.13 g DI water were charged into a 2 L flask equipped with a stirrer, a condenser, and a thermocouple in a cooling bath. 252.1 g 1,6-hexamethylenediisocyanate (HDI) was added into the reaction mixture to maintain temperature below 30° C. by using a cooling bath. After finishing addition of HDI, the reaction mixture was allowed to stand at room temperature until the NCO peak was gone as evidenced by IR (2260 cm-1). A clear solution was obtained.

Example 2

Synthesis of 1,1,6,6-hexamethylene-3,3,3',3'-tetrakis (2-hydroxypropyl)-bis-urea 199.8 g diisopropanolamine and 299.7 g DI water were charged into a 2 L flask equipped with a stirrer, a condenser, and a thermocouple in a cooling bath. 126.1 g 1,6-hexamethylenediisocyanate (HDI) was added into the reaction mixture to maintain temperature below 30° C. by using a cooling bath. After finishing addition of HDI, the reaction mixture was allowed to stand at room temperature until the NCO peak was gone as evidenced by IR (2260 cm-1). A clear solution was obtained.

Example 3

Synthesis of Tetrakis(2-hydroxyethyl)-bis-urea from IPDI 315.4 g diethanolamine and 552 g DI water were charged into a 2 L flask equipped with a stirrer, a condenser, and a thermocouple in a cooling bath. 333.4 g isophorone diisocyanate (IPDI) was added into the reaction mixture to maintain temperature below 30° C. by using a cooling bath. After finishing addition of IPDI, the reaction mixture was allowed to stand at room temperature until the NCO peak was gone as evidenced by IR (2260 cm$^{-1}$). A clear solution was obtained.

Example 4

Synthesis of Tetrakis(2-hydroxypropyl)-bis-urea from IPDI 199.8 g diisopropanolamine and 299.7 g DI water were charged into a 2 L flask equipped with a stirrer, a condenser, and a thermocouple in a cooling bath. 166.7 g isophorone diisocyanate (IPDI) was added into the reaction mixture to maintain temperature below 30° C. by using a cooling bath. After finishing addition of IPDI, the reaction mixture was allowed to stand at room temperature until the NCO peak was gone as evidenced by IR (2260 cm$^{-1}$). A clear solution was obtained.

Example 5

Synthesis of HAU from HDI Trimer 105.1 g diethanolamine and 315.4 grams of DI water were charged into a 1 L flask equipped with a stirrer, a condenser, and a thermocouple in a cooling bath. 193.4 g DESMODUR N3300A (HDI trimer) was added into the reaction mixture to maintain temperature below 30° C. by using a cooling bath. After finishing addition of HDI trimer, 105.1 g DOWANOL PM was used to rinse the addition funnel. The reaction mixture was allowed to stand at room temperature until the NCO peak was gone as evidenced by IR (2260 cm$^{-1}$). A clear solution was obtained.

Example 6

Synthesis of HAU from HDI Trimer 166.5 g diisopropanolamine and 333 grams of DI water charged into a 1 L flask equipped with a stirrer, a condenser, and a thermocouple in a cooling bath. 214.25 grams of DESMODUR N3300A (HDI trimer) was added into the reaction mixture to maintain temperature below 30° C. by using a cooling bath. After finishing addition of HDI trimer, 300 grams of Dowanol PM was used to rinse the addition funnel. The reaction mixture was allowed to stand at room temperature until the NCO peak was gone as evidenced by IR (2260 cm$^{-1}$). A clear solution was obtained.

Example 7

Synthesis of HAU from IPDI Trimer 105.1 g diethanolamine, 262.9 grams of DI water, and 157.7.6 g DOWANOL PM were charged into a 1 L flask equipped with a stirrer, a condenser, and a thermocouple in a cooling bath. A solution of 242.8 g IPDI trimer in 242.8 g MIBK was added into the reaction mixture to maintain temperature below 20° C. by using a cooling bath. After finishing addition of IPDI trimer, 10 g Dowanol PM was used to rinse the addition funnel. The reaction mixture was allowed to stand at room temperature until the NCO peak was gone as evidenced by IR (2260 cm$^{-1}$). A clear solution was obtained.

Example 8

Synthesis of HAU from IPDI Trimer 133.2 g diisopropanolamine, 199.7 grams of DI water, and 236.6 g DOWANOL PM were charged into a 1 L flask equipped with a stirrer, a condenser, and a thermocouple in a cooling bath. 360 g DESMODUR Z 4470 BA (IPDI trimer in butyl acetate) was added into the reaction mixture to maintain temperature below 30° C. by using a cooling bath. After finishing addition of IPDI trimer, 100 g DOWANOL PM was used to rinse the addition funnel. The reaction mixture was allowed to stand at room temperature until the NCO peak was gone as evidenced by IR (2260 cm$^{-1}$). A clear solution was obtained.

Example 9

Coating Compositions

Example 9A

A OH terminated polyurethane was prepared by the following procedure. 100 g of 2-ethylhexyl acrylate (EHA), 79.2 g of hydroxyethyl methacrylate (HEMA), 1.5 g of 2,6-di-tert-butyl 4-methyl phenol, 0.78 g of triphenyl phosphite, 0.78 g of dibutyl tin dilaurate, 405 g of polytetrahydrofuran with number average molecular weight 1000, 81.6 g of dimethyol propionic acid, and 4 g of triethyl amine were charged in order into a four necked round bottom flask fitted with a thermocouple, mechanical stirrer, and condenser. The mixture was heated to 90° C. and held for 15 minutes. After that, 405.5 g of isophorone diisocyanate was charged into the flask over 90 minutes. After that, the isocyanate addition funnel was rinsed with 20 g of 2-ethylhexyl acrylate. The mixture was held at 90° C. until all of the isocyanate IR peak was gone. After that, 454 g of 2-ethylhexyl acrylate and 72.5 DOWANOL PM were charged into flask, and cooled to ambient temperature. The acid value of the polyurethane was measure to be 23.5 mg KOH/g, and weight average molecular weight by GPC was 7269.

Example 9B

A carboxyl functionalized polyurethane/acrylic latex was prepared as follows. 545 g of deionized water, 15.6 g of AEROSOL OT-75 from Cytec, 10.7 g of dimethyl ethanolamine, 298 g of the OH terminated polyurethane prepared according to Example 9A, 74.4 g of methyl methacrylate, and 11.1 g of hexanediol diacrylate was charged in order to a four necked round bottom flask fitted with a thermocouple, mechanical stirrer, and condenser. The mixture was heated to 33° C. and held for 30 minutes with a N$_2$ blanket. After that, a mixture of 0.38 g of t-butylhydroperoxide and 15 g of deionized water was charged into the flask, and mixed for 15 minutes. A mixture of 0.008 g ferrous ammonium, sulfate, 0.38 g sodium metabisulfite and 15 g of deionized water was charged into the flask over 30 minutes. During this charge, exotherm was expected. After peak exotherm, the system was held at 65° C. for 1 hour. After it was cooled to 45° C., 3.5 g of aciticide MBS from Thor GmbH, 0.18 g of FOAMKILL 649 from Crucible Chemical, and 1.5 g of deionized water were charged into flask and mixed for 15 minutes.

The resulting latex had a solid content of 38.5%, and the volume average particle size measured by Zetasizer was 104 nm.

Example 10

Different hydroxyl functional alkyl polyureas of the present invention were mixed with the acid functional polymer of Example 9B at a COOH/OH ratio of 1/1. The mixture was drawn down to panel with a wet thickness of 100 micrometer. The film was dried at room temperature for 15 minutes, and followed by baking at different temperatures for 30 minutes. After cooling at room temperature for 30 minutes, panels were tested for MEK double rubs. Into separate samples of solution containing the polymer of 9B and the hydroxyl functional alkyl polyureas was added 1% TYZOR LA (catalyst, available from Dorf Ketal Chemical, LLC). This solution was drawn down on a panel, followed by a 30 minutes bake at different temperatures and tested for MEK double rubs.

As shown in the following Table 1, when TYZOR LA was used, MEK double rubs were significantly higher than samples without the catalyst particularly at 130° C.

TABLE 1

| Hydroxyl functional alkyl polyurea | TYZOR LA | MEK double rubs | |
|---|---|---|---|
| | | cure at 130° C. | cure at 140° C. |
| Example 1 | 0 | 35 | 90 |
| Example 1 | 1% | 130 | 150 |
| Example 2 | 0 | 30 | 80 |
| Example 2 | 1% | 110 | 150 |
| Example 3 | 0 | 40 | 80 |
| Example 3 | 1% | 110 | 150 |
| Example 4 | 0 | 40 | 70 |
| Example 4 | 1% | 70 | 150 |
| Example 5 DEA/HDI trimer | 0% | 35 | 70 |
| Example 5 DEA/HDI trimer | 1% | 110 | 150 |
| Example 6 DIPA/HDI trimer | 0% | 30 | 80 |
| Example 6 DIPA/HDI trimer | 1% | 90 | 150 |
| Example 7 DEA/IPDI trimer | 0% | 30 | 70 |
| Example 7 DEA/IPDI trimer | 1% | 35 | 110 |
| Example 8 DIPA/IPDI trimer | 0% | 20 | 60 |
| Example 8 DIPA/IPDI trimer | 1% | 60 | 110 |

Example 11

Polyurea Example 1 and acid functionalized PU/acrylate (example 9B) were mixed at a COOH/OH ratio of 1/1, and different catalyst as shown below (1% based on mixture) were mixed in. The mixtures were then drawn down to panel with a wet thickness of 100 micrometer. The film was dried at room temperature for 15 minutes, and followed by baking at different temperature for 30 minutes. After cooling at room temperature for 30 minutes, panels were tested for MEK double rubs.

As shown in the following Table 2, TYZOR LA, TYZOR 131 (catalyst, available from Dorf Ketal Chemical, LLC), and DBTDL performed better than control without catalyst.

TABLE 2

| Catalyst | catalyst level | MEK double rubs |
|---|---|---|
| none | 0 | 35 |
| TYZOR LA | 1% | 130 |
| TYZOR 131 | 1% | 70 |
| DBTDL | 1% | 100 |

Example 12

Polyurea Example 1 and TYZOR LA (1% based on mixture) were mixed with acid functionalized PU/acrylate (example 9B) at a COOH/OH ratio of 1/1. The mixture was then drawn down to panel with a wet thickness of 100 micrometer. The film was dried at room temperature for 15 minutes, and followed by baking at different temperatures for 30 minutes. After cooling at room temperature for 30 minutes, panels were tested with different solvent for double rubs.

As shown in the following Table 3, with 1% TYZOR as catalyst, film resistance to solvents are significantly better than film without catalyst.

TABLE 3

| TYZOR LA | 0 | | 1.00% | |
|---|---|---|---|---|
| Cure T (° C.) | 130 | 140 | 130 | 140 |
| acetone | 20 | 70 | 70 | 150 |
| DOWANOL PM | 20 | 80 | 60 | 150 |
| MEK | 40 | 110 | 130 | 150 |
| butyl acetate | 150 | 130 | 150 | 150 |
| A100 | 120 | 150 | 150 | 150 |
| hexane | 150 | 150 | 150 | 150 |
| water | 150 | 150 | 150 | 150 |

Example 13

Beverage can Overvarnish Cured with HAU

The coating of Example 13 was prepared by combining all of the materials shown in Table 4 and mixing for 10 minutes with a mixing blade.

TABLE 4

| Material | Description | Amount |
|---|---|---|
| Water reducible acrylic (255 acid value on 100% solids) | Acrylic resin* | 190.43 |
| DI Water | De-ionized water | 18.0 |
| DIPA/HDI trimer (Example 6) | HAU crosslinker | 107.94 |
| Tyzor LA | Organic titanate from Dorf Ketal | 1.99 |
| BYK-333 | Slip agent from BYK | 0.3 |
| Total | | 318.66 |

*An acrylic resin was prepared according to the procedures outlined by Hellring in Example 1 of United States Patent Application Publication Number 2015/0280239 A1.

Coated panels were obtained by drawing the coating over chrome treated 5182-H48 aluminum panels using a wire wound rod to obtain dry coating weights of 2.0-2.5 mg/square inch (msi). The coated panels were immediately placed into a one-zone, gas-fired, conveyor oven for 15 seconds and baked to a peak metal temperature of 400° F. (204° C.) or 320° F. (160° C.). The baked panels were immediately tested for hot tack cure test.

In the hot tack cure test, the minimum cure temperature was determined for a film to achieve resistance to damage when rubbed at an elevated temperature and compared to a control.

Once the panel exited the oven, the panel was immediately placed on a 60° C. hot plate. Typically the hot plate temperature is controlled to mimic the can temperature as measured at the "deco oven" exit on a commercial can line. Using a gauze (4"×4"-12 ply gauze pad) covered 2 lb. hammer, the panel was held against the hot plate for at least 5 seconds. Resting the gauze covered hammer head on the panel, the coated surface was double rubbed 5 times. The tack resistance was rated for mar resistance.

TABLE 5

| | Example 13 | | PPG3805803 Waterborne Overvarnish from PPG | |
|---|---|---|---|---|
| 1st Bake (PMT) | 204° C. | 160° C. | 204° C. | 160° C. |
| 60° C. Hot Tack Test Mar Rating | None (Pass) | None (Pass) | Very Slight (Pass) | Severe (Fail) |

A second bake was subsequently applied to the panel to simulate an inside spray bake and to obtain the final properties of the overvarnish. The baked panel from the gas conveyor oven was placed in a 204° C. box oven for 3 minutes. The panels were cooled down and evaluated for MEK double rubs and Joy Detergent tests.

The MEK double rub test rub used a gauze covered hammer that was saturated with methyl ethyl ketone. The coatings were evaluated for the number of double rubs it took to soften and break through the coating or until 50 double rubs were performed. The coatings were also evaluated for their ability to adhere to the aluminum panels and to resist blushing in the Joy detergent test. The results of the test are reported in Table 2.

Blush Resistance: Blush resistance measured the ability of a coating to resist attack by various testing solutions. When the coated film absorbs test solution, it generally becomes cloudy or looks white. Blush was measured visually using a scale of 1-10 where a rating of "10" indicates no blush and a rating of "0" indicates complete whitening of the film. Blush ratings of at least 6 are typically desired for commercially viable coatings. The coated panel tested was 2×4 inches (5×10 cm) and the testing solution covered half of the panel being tested so you can compare blush of the exposed panel to the unexposed portion.

Adhesion: Adhesion testing was performed to assess whether the coating adheres to the substrate. The adhesion test was performed according to ASTM D 3359 Test Method B, using Scotch 610 tape, available from 3M Company of Saint Paul, Minn. Adhesion was generally rated on a scale of 1-10 where a rating of "10" indicates no adhesion failure, a rating of "9" indicated 90% of the coating remains adhered, a rating of "8" indicates 80% of the coating remained adhered, and so on.

Joy Detergent Test: The "Joy" test measured the resistance of a coating to a hot 82° C. Joy detergent solution. The solution was prepared by mixing 30 grams of Ultra Joy Dishwashing Liquid (product of Procter & Gamble) into 3000 grams of deionized water. Coated strips were immersed into the 82° C. Joy solution for 15 minutes. The strips were then rinsed and cooled in deionized water, dried, and immediately rated for blush as described previously.

TABLE 6

| | Bake Conditions | MEK Double Rubs | Joy Detergent Test Blush/Adhesion |
|---|---|---|---|
| Example 1 | 1st Bake: 15" @ 400 F. PMT<br>2nd Bake: 3'@400 F. | 50 | 10/10 |
| Example 1 | 1st Bake: 15" @ 320 F. PMT<br>2nd Bake: 3'@400 F. | 50 | 10/10 |
| PPG3805803* | 1st Bake: 15" @ 400 F. PMT<br>2nd Bake: 3'@400 F. | 50 | 10/10 |
| PPG3805803* | 1st Bake: 15" @ 320 F. PMT<br>2nd Bake: 3'@400 F. | 50 | 10/10 |

*PPG 3805803 is a commercial water reducible varnish from PPG Industries. It contains two water reducible acrylic resins and melamine (formaldehyde containing)

Example 14

The hydroxyl functional alkyl polyureas of Example 1 and Example 3 were each mixed with an acrylic latex polymer that had a solid content of 29.8% when measured after heating a sample to 110° C. for 1 hour and a measured acid value of 12.8 mg KOH/g. The acrylic latex was prepared according to the procedures outlined by Perez in Example 18 of U.S. Pat. No. 5,714,539. The crosslinkers of Example 1 and Example 3 were added in various amounts to achieve different ratios of COOH/OH as indicated in Table 7. To the mixtures were added 10% on solids of ethylene glycol mono-2-ethylhexyl ether (purchased from Eastman as Ektasolve EEH). The mixtures were drawn down on 0.0082" aluminum substrate to a wet film thickness of 37 microns. The film was baked for 10 seconds in a 290° C. conveyor oven. The substrate reached a Peak Metal Temperature of 232.2° C.

After baking, the cured coatings were tested for solvent resistance using the "MEK Double Rub" test described in Example 13. The cured coating was also evaluated with the Acetic Acid Test. The Acetic Acid Test measured the resistance of the coating to a boiling 3% acetic acid solution. The solution was prepared by mixing 90 g of glacial acetic acid (product of Fisher Scientific) into 3000 g of deionized water. Coated strips were immersed into the boiling acetic acid solution for 30 minutes. The strips were then rinsed and cooled in deionized water, dried, and immediately rated for blush. Blush was measured and reported in Example 13.

As shown in the following Table 7, the solvent resistance (MEK DR) and the blush results (Acetic Acid Blush) were better when the hydroxyl alkyl functional polyurea was used.

TABLE 7

| 232.2° C. Peak Metal Temperature | | | |
|---|---|---|---|
| COOH/OH Ratio | | MEK DR | Acetic Acid Blush |
| — | none | 16 | 4 |
| 1:0.35 | IPDI/DEA | 68 | 6 |
| 1:0.55 | Example 3 | 100 | 7 |
| 1:0.9 | | 100 | 6 |
| 1:0.35 | HDI/DEA | 94 | 6 |
| 1:0.55 | Example 1 | 100 | 6 |
| 1:0.9 | | 100 | 6 |

In a second series of tests, the mixtures described above were drawn down on 0.0082" aluminum substrate to a wet film thickness of 37 microns. The film was baked for 10 seconds in a 267° C. conveyor oven. The substrate reached a Peak Metal Temperature of 215.6° C.

After baking, the cured coatings were checked for solvent resistance using the MEK double rub test. As shown in the following Table, the MEK Double Rubs results improve with the inclusion of the hydroxyl alkyl functional polyurea as compared to no HAU.

TABLE 8

| 215.6° C. Peak Metal Temperature | | |
|---|---|---|
| COOH/OH Ratio | | MEK DR |
| — | none | 14 |
| 1:0.35 | IPDI/DEA | 56 |
| 1:0.55 | Example 3 | 39 |
| 1:0.9 | | 57 |
| 1:0.35 | HDI/DEA | 58 |
| 1:0.55 | Example 1 | 54 |

Example 15

Vibration Damping Composition

Coating compositions were prepared by mixing ingredients shown in the table below in a SpeedMixer™ DAC 600.1 FVZ mixer which is available from FlackTek, Inc. Components 1-8 were weighed in a DAC mixing cup in the order shown in the table and mixed for one minute at 2350 rpm. Then components 9-15 were added in the order shown in the table and mixed for one minute at 2350 rpm. The cup was then scraped with a spatula to remove materials on the interior wall of the cup. The components were mixed again for one minute at 2350 rpm. After this final mix, the coating compositions were ready for testing.

TABLE 9

| | Example 15A | Example 15B |
|---|---|---|
| Acrylic latex[1] | 28.31 | 28.11 |
| Urethane diol[2] | 1.00 | 1.00 |
| DIPA/HDI trimer[3] | — | 1.11 |
| Dibutyltin dilurate[4] | — | 0.06 |
| Idropon Logic 30[5] | 0.06 | 0.06 |
| BYK 032[6] | 0.10 | 0.10 |
| Propylene Glycol[7] | 0.99 | 0.98 |
| Santicizer 278[8] | 1.15 | 1.14 |
| Silene 732D[9] | 1.86 | 1.85 |
| Extendospheres TG[10] | 1.65 | 1.64 |
| Expancel 551 DU 40[11] | 0.10 | 0.10 |
| Dolocron 4512[12] | 39.51 | 39.22 |
| NYAD M325[13] | 22.63 | 22.47 |
| Rheology modifier[14] | 1.51 | 1.50 |
| Acrysol RM-12W[15] | 1.12 | 0.67 |
| | 100.00 | 100.00 |

[1]Acrylic latex with 50° C. Tg, available from PPG Industries, Inc.
[2]Reaction product of propylene carbonate and Jeffamine D400
[3]Example 6
[4]Available from PMC Group
[5]Dispersion Available from Macri Chemicals
[6]Defoamer available from BYK Chemie
[7]Available from Dow Chemical
[8]Alkyl benzyl phthalate from Ferro Corp.
[9]Silica available from PPG
[10]Glass beads available from Sphere one Inc.
[11]Polymeric hollow particles available from Akzo Nobel Chemicals
[12]Mineral filler available from Specialty Minerals
[13]Mineral fillers available from NYAD Minerals
[14]Dispersion of Hydroxypropylcellulose Klucel G in water at 15 to 85 weight ratio
[15]Urethane rheology modifier available from Dow Chemical A 10×10 inch draw down of the coating using a 120-mil thick template was prepared on electro-coated steel panel. After 30 minutes air dry at ambient temperature the panel was placed in a wood box for baking. The box had a circular hole of 3-inch diameter on the side facing the backside of the panel. The box with the panel was then placed in a 149° C. convection oven for 30 minutes. The box was placed in a way that the hole would face the direction of air flow in the oven during the bake process.

The box was removed from the oven after 30 minutes and the panel was taken out the box. After cooling to ambient temperature, appearance of the panel was visually examined. The panel coated with the composition of example 15A, without the HAU, had multiple long and deep cracks close to the edges on all four sides. The panel coated with the composition of example 15B had shallow cracks along one side and some short and shallow cracks on two other sides of the panel. The remaining side had little to no cracks.

Example 16

Latex Formation

An isocyanate terminated polyurethane was prepared by the following procedure. 134.5 g of butyl acrylate, 108.2 g of FORMREZ 66-56 from Chemtura, 108.2 g of POLYMEG 2000 from BASF, 0.8 g of 2,6-di-tert-butyl 4-methyl phenol, 10.3 g of hydroxyethyl methacrylate (HEMA), 35 g of dimethyol propionic acid (DMPA), and 1.6 g of triethyl amine were charged into a four necked round bottom flask fitted with a thermocouple, mechanical stirrer, and condenser. The mixture was heated to 50° C. and held for 15 minutes. After that, 130 g of isophorone diisocyanate was charged into the flask over 10 minutes, and mixed for 15 minutes. 9.7 g of butyl acrylate and 0.4 g of dibutyl tin dilaurate (DBTDL) was charged into flask. Immediate exotherm was observed. After exotherm subsided, the mixture was heated to 90° C., and held for 60 minutes. The NCO equivalent weight was measured to be 1705. After that, the mixture was cooled to 70° C., and 134.5 g of butyl acrylate and 23.5 g of hexanediol diacrylate were charged into the flask. The mixture was kept at 60° C., until dispersed into water.

A polyurethane acrylic latex with HAU functional groups attached on the shell was prepared as follows. 1030 g of deionized water, 22.8 g of dimethyl ethanolamine, 5.0 g of ethyl diamine, and 13.5 g diethanolamine were charged into a four necked round bottom flask fitted with a thermocouple, mechanical stirrer, and condenser. The mixture was heated to 50° C. and held for 30 minutes with N2 blanket. After that, 650 g of isocyanate terminated polyurethane made above was dispersed into the flask over 20 minutes, and mixed for additional 15 minutes. A mixture of 1.9 g of ammonium persulfate and 41.3 g deionized water was charged into flask over 15 minutes. The temperature rose from 50° C. to 69° C. due to polymerization exotherm. After that, latex was held at 75° C. for additional 1 hour. After it was cooled to 40° C., 0.3 g of FOAMKILL 649, 5.8 g of ACTICIDE MBS, and 14 g of deionized water were charged and mixed for additional 15 minutes. The resulting latex was filtered via 10 μm bag. The resulting latex had a solid content of 38.3%, and the volume average particle size measured by Zetasizer was 69 nm.

As a curing performance test, 1 g Tyzor LA was mixed with 100 g of the above latex. The mixture was drawn down to panel with a wet thickness of 100 micrometer. The film was dried at room temperature for 15 minutes, followed by baking at 120° C. for 30 minutes. After cooling at room temperature for 30 minutes, panels were tested for MEK double rubs. The MEK double rub for the panels coated with the latex composition of the present invention was >150.

Example 17

Formaldehyde Free Wood Fiberboard

A composition according to the present invention was prepared by combining all the materials shown in Table 10 and mixing for 10 minutes in a paint shaker.

TABLE 10

| Material | Amount (grams) |
| --- | --- |
| Composition preparation | |
| Acrylic resin (50/40/10 BA/MMA/AA) | 200.00 |
| DI Water | 60.56 |
| DIPA/HDI trimer from Example 6 | 20.13 |
| Total | 280.69 |
| Fiberboard preparation | |
| Composition from table 10 | 3.4 |
| Wood and wood dust | 3.4 |
| Total | 6.8 |

The composition in Table 10 was mixed with the wood and wood dust in an 8 oz. plastic container using a centrifuge for 30 s to ensure proper soaking of the wood dust by the composition. Mixed samples were then put between two metal plates wrapped in Tedlar and held in a heated Carver Press (350° F. at 1000 psi for 50 s) to form a fiberboard. The fiberboard sample was visually inspected and hand flexed/bent to demonstrate mechanical strength; no tear was observed and the integrity of the sample was noted.

Example 18

OEM Basecoat

One grey basecoat was prepared from the following mixture of ingredients:

| Components | Parts by weight of Component |
| --- | --- |
| HAU latex[1] | 202.05 |
| acrylic latex[2] | 43.21 |
| Byk 348 surfactant[3] | 0.3 |
| Byk 032 defoamer[4] | 1.85 |
| Surfynol 104E[5] | 4 |
| 50% DMEA[6] | 2.68 |
| Mineral Spirits[7] | 3 |
| White Tint[8] | 31.85 |
| Black Tint[9] | 20.32 |
| Yellow Tint[10] | 9.06 |
| Urethane Diol[11] | 6.01 |
| Dowanol PnB[12] | 3 |
| 2-ethylhexanol[13] | 7 |
| Tyzor LA Titanate | 2 |

-continued

| Components | Parts by weight of Component |
|---|---|
| Byketol WS surface additive[14] | 7.76 |
| Deionized Water | 4.16 |
| Total | 348.25 |

[1] HAU latex from Example 16
[2] A core-shell acrylic latex made by PPG
[3,4,14] Commercially available from Byk Chemie
[5] Surfactant commercially available from Air Products and Chemicals, Inc.
[6] Dimethyl ethanolamine 50% aqueous solution
[7] Solvent available from Shell Chemical Co.
[8] White tint paste consisting of 61% TiO2 dispersed in 9% acrylic polymer blend having a solids content of 70%
[9] Black Tint paste consisting of 6% carbon black dispersed in 18% acrylic polymer and having a solids content of 24%
[10] Yellow Tint paste consisting of 25% Mapico Yellow 1050A dispersed in 21% acrylic polymer and having a solids content of 46%
[11] Polyurethane diol prepared by reacting 1 mole of Jeffamine D-400 (from Huntsman Chemical Co.) with 2 moles of ethylene carbonate at 130° C. according to the procedure generally set forth in U.S. Pat. No. 7,288,595.
[12] Propylene glycol n-butyl ether commercially available from Dow Chemical Co.
[13] Solvent commercially available from Dow Chemical Co.

The basecoat was spray applied in an environment controlled to 70-75° F. (21-24° C.) and 50-60% relative humidity onto 4 inch by 12 inch (10 cm by 30 cm) steel panels that were coated with PPG Electrocoat (ED6100C) commercially available from PPG Industries, Inc. The substrate panels were obtained from ACT Test Panels, LLC of Hillsdale, Mich. The basecoat was applied in two coats, with a 5 minutes ambient flash between coats, and then flashed at ambient temperature for 5 minutes and then dehydrated for 5 minutes at 185° F. (85° C.). The film thickness was approximately 1.2 mils (30 microns). A 2K clearcoat commercially available from PPG Industries, Inc. as TKAPO1000 was then applied over the basecoated panels in two coats with 90 seconds ambient flash between coats. The clearcoated panels were allowed to flash for 10 minutes at ambient conditions and baked for 30 minutes at 285° F. (140° C.). The film thickness was approximately 1.8 mils (45 microns).

Appearance and physical properties were measured on coated panels.

| | BYK Wavescan[17] | | | DOI after humidity resistance[19] | |
|---|---|---|---|---|---|
| Fischer Microhardness[16] | Long Wave | Short Wave | initial DOI[18] | 1 hour Recovery | 24 hours Recovery |
| 125.8 | 9.8 | 39.9 | 95 | 95 | 95 |

[16] HM2000 Fischer Microhardness instrument manufactured by Fischer
[17] BYK Wavescan instrument manufactured by BYK Gardner USA of Columbia, Maryland
[18] Distinctness of Image (DOI) meter manufactured by TRICOR Systems, Inc. of Elgin, Illinois.
[19] Ten day humidity resistance test similar to ASTM D1735-92 conducted in a Harshaw Equipment GS "Uni-Fog" corrosion test cabinet set at 100° F. (38° C.) and 100% relative humidity. DOI measured after 1 hour and 24 hours recovery time after completion of test.

As can be seen in the above table, a composition according to the present invention, when used in a wet-on-wet application retained its DOI after a ten day humidity resistance test.

Example 19

Each of the components listed in the table below were weighed in a container and mixed in a prism high speed mixer for 30 seconds at 3500 RPM to form a dry homogeneous mixture. The mixture was then melt-mixed in a Werner Pfleiderer 19 mm twin screw extruder with an aggressive screw configuration and a speed of 500 RPM. The first zone was set at 50° C., and the second, third, and fourth zones were set at 110° C. The feed rate was such that a torque of 55-65% was observed on the equipment. The mixtures were dropped onto a set of chill rolls to cool and re-solidify the mixtures into solid chips. The chips were milled in a Mikro ACM®-1 Air Classifying Mill to obtain a particle size of 5 to 90 microns with a majority of the particles being from 20 to 50 microns and an average particle size of approximately 27 microns. The resulting coating compositions for each of Example 19 were solid particulate powder coating compositions that were free flowing.

| Component | Ex. 19A (gram) | Ex. 19B (gram) |
|---|---|---|
| Rucote 9010 [1] | 68.58 | 70.51 |
| RESIFLOW ® PL-200A[2] | 0.94 | 0.96 |
| Uraflow B [3] | 0.61 | 0.61 |
| Licowax C [4] | 0.61 | 0.61 |
| Imide epoxy urethane [5] | 0.25 | 0.25 |
| Tiona 696 TiO$_2$ [6] | 5.44 | 5.44 |
| Bayferrox 1420M [7] | 16.12 | 16.12 |
| Primid XL-552[8] | 3.31 | 3.40 |
| Licocene Pe1MA435[9] | 1.15 | 1.15 |
| HAU[10] | 2.00 | — |
| Crayvallac Super [11] | 1.00 | — |

[1] An acid functional polyester with an acid number of 28, commercially available from Stepan Company.
[2] Acrylic/silica flow and leveling control agent, commercially available from Estron Chemical.
[3] Benzoin, commercially available from Mitsubishi Chemical Corp.
[4] Ethylene Bis(stearamide), commercially available from Clariant Corporation.
[5] Imide hydroxyl urethane additive produced internally by PPG Industries.
[6] Titanium dioxide pigment commercially available from Cristal global.
[7] Yellow iron oxide commercially available from OMG.
[8] Hydroxy alkylamide commercially available from EMS-American Grilon Inc.
[9] Metallocene wax commercially available from Clariant Corp.
[10] 399.6 g diisopropanolamine and 799.1 grams of Dowanol PM were charged into a 3 L flask equipped with a stirrer, in a a condenser, and a thermocouple in a cooling bath. The reaction mixture was cooled to 10° C. by using ice bath. 579 grams of DESMODUR N3300A (HDI trimer) was added into the reaction mixture to maintain temperature below the 35° C. After finishing the addition of HDI trimer, 79.9 grams of Dowanol PM was used to rinse the addition funnel. The reaction mixture was allowed to stand at room temperature until the NCO peak was gone as evidenced by IR (2260 cm$^{-1}$) (IR spectrometer, ThermoScientific Nicolet iS5 FT-IR). After completion of the reaction, the reaction mixture was concentrated by evaporation under vacuum to remove solvent. The residual liquid was poured out onto aluminum foil and formed a solid at room temperature.
[11] Modified amide wax commercially available from Arkema Inc.

Example 20

Application of Solid Particulate Powder Coatings

The powder coating compositions of Example 19 were applied at a thickness of 40 microns to 90 microns front and back onto a nitrogen laser cut hot rolled multi-edge steel test coupon having the cut-outs and edges as shown in FIG. 1.

The powder coating was applied with a Versa-Spray II Nordson powder coating gun at 60 kv with a vibratory feed dispenser with 15 psi atomizing and 15 psi flow air. The coating was cured for at 375° F. for about 20 to 35 minutes to form a coating layer. Edge coverage was tested by taping over the bottom half of the ¼ inch hole at the top of the test coupon with 1 inch tape and leaving ~71 mm from top to bottom of the test coupon available to measure edge exposure. Paint above the taped area was removed to allow a connection to the bare metal. Edge exposure was measured with a WACO Enamel Rater by immersing the test coupon down to the tape area into a 1% by weight NaCl salt solution in deionized water in an open steel IL container. An electrical connection was made with the metal container and the test coupon. A current was then passed through the test coupon for 4 seconds and the peak amperage was recorded. Lower amperage values means less exposed edges and better edge coverage. Example 19A formulated with HAU gave a much more favorable enamel rating then the comparative Example 19B, made without HAU.

| Testing Property | Ex. 19A | Ex. 19B |
|---|---|---|
| Enamel Rater (mA) | 115 | 434 |
| GPF (mm) | 19 | 21 |
| 20°Gloss | 91 | 91 |

Whereas particular embodiments of this invention have been described above for purposes of illustration, it will be evident to those skilled in the art that numerous variations of the details of the present invention may be made without departing from the invention as defined in the appended claims.

BRIEF DESCRIPTION OF THE DRAWINGS

FIG. 1 illustrates the cut outs and edges on a nitrogen laser cut hot rolled multi-edge steel test coupon.

What is claimed is:

1. A composition that comprises a compound having a hydroxy functional alkyl polyurea and/or hydroxy functional alkyl polyurea moiety having the formula:

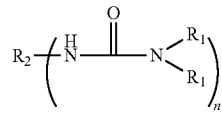

wherein $R_2$ comprises a substituted or unsubstituted $C_1$ to $C_{36}$ alkyl group, an aromatic group, an isocyanurate moiety, biuret moiety, allophonate moiety, glycoluril moiety, benzoguanamine moiety, polyetheramine moiety, and/or polymeric moiety different from a polyetheramine and having an Mn of 500 or greater; wherein each $R_1$ is independently a hydrogen, alkyl having at least 1 carbon, or a hydroxy functional alkyl having 2 or more carbons and at least one $R_1$ is a hydroxy functional alkyl having 2 or more carbons; and n is 2-6; wherein the polyurea is present in the composition in an amount of 0.5 to 10 weight percent based on total solid weight.

2. The composition of claim 1, wherein $R_2$ comprises an isocyanurate moiety.

3. The composition of claim 1, wherein at least one $R_1$ comprises a 2-hydroxyethyl or 2-hydroxypropyl group.

4. A composition comprising
   a. a film-forming resin;
   b. a crosslinker that reacts with the film-forming resin; and
   c. a compound having a hydroxy functional alkyl polyurea and/or hydroxy functional alkyl polyurea moiety having the formula

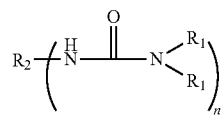

wherein $R_2$ comprises a substituted or unsubstituted $C_1$ to $C_{36}$ alkyl group, an aromatic group, an isocyanurate moiety, biuret moiety, allophonate moiety, glycoluril moiety, benzoguanamine moiety, polyetheramine moiety, and/or polymeric moiety different from a polyetheramine and having an Mn of 500 or greater; wherein each $R_1$ is independently a hydrogen, alkyl having at least 1 carbon, or a hydroxy functional alkyl having 2 or more carbons and at least one $R_1$ is a hydroxy functional alkyl having 2 or more carbons; and n is 2-6.

5. The composition of claim 4, wherein $R_2$ comprises a substituted or unsubstituted $C_2$-$C_{12}$ alkyl or aromatic group.

6. The composition of claim 4, wherein $R_2$ comprises a substituted or unsubstituted $C_6$ alkyl group.

7. The composition of claim 4, wherein $R_1$ comprises a 2-hydroxyethyl or 2-hydroxypropyl group.

8. The composition of claim 4, wherein the composition is substantially formaldehyde free.

9. The composition of claim 4, wherein the film-forming resin is an acid functional polyester resin.

10. The composition of claim 4, wherein the crosslinker comprises hydroxy alkyl amide.

11. The composition of claim 4, wherein the composition is formulated as a sound damping composition.

12. The composition of claim 4, wherein the $R_1$ groups do not contain an ether linkage.

13. The composition of claim 4, wherein the film forming resin comprises a polyolefin dispersion.

14. The composition of claim 4, wherein the composition is formulated as a coating.

15. The composition of claim 14, wherein the coating is a powder coating.

16. The composition of claim 4, further comprising a catalyst.

17. The composition of claim 16, wherein the catalyst comprises tin and/or titanium.

18. A substrate coated at least in part with the composition of claim 4.

19. The substrate of claim 18, wherein the substrate comprises a package.

20. The substrate of claim 18, wherein the substrate comprises a metal can.

21. The substrate of claim 18, wherein the substrate comprises a vehicle.

22. The substrate of claim 18, wherein the substrate is rubber and/or plastic.

23. The substrate of claim 18, wherein the substrate comprises a metal sheet or coil.

24. A polymer or oligomer comprising a repeat unit having a hydroxy functional alkyl polyurea of the formula:

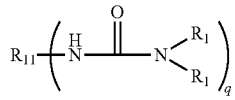

wherein $R_{11}$ is derived from a polymerizable moiety; wherein each $R_1$ is independently a hydrogen, an alkyl having at least 1 carbon, or a hydroxy functional alkyl having 2 or more carbons and at least one $R_1$ is a hydroxy functional alkyl having 2 or more carbons; and q is 1 or greater.

25. A composition comprising the polymer of claim 24.

26. The composition of claim 25, wherein $R_{11}$ has acid functionality to form a latex.

27. A substrate formed from a composition comprising:
a) A composition that comprises a compound having a hydroxy functional alkyl polyurea and/or hydroxy functional alkyl polyurea moiety having the formula:

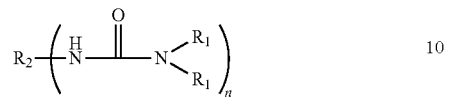

wherein $R_2$ comprises a substituted or unsubstituted $C_1$ to $C_{36}$ alkyl group, an aromatic group, an isocyanurate moiety, biuret moiety, allophonate moiety, glycoluril moiety, benzoguanamine moiety, polyetheramine moiety, and/or polymeric moiety different from a polyetheramine and having an Mn of 500 or greater; wherein each $R_1$ is independently a hydrogen, alkyl having at least 1 carbon, or a hydroxy functional alkyl having 2 or more carbons and at least one $R_1$ is a hydroxy functional alkyl having 2 or more carbons; and n is 2-6; and
b) wood particles.

* * * * *